(12) United States Patent
Bharti et al.

(10) Patent No.: US 10,653,823 B2
(45) Date of Patent: May 19, 2020

(54) WOUND DRESSING WITH MICROPUMP

(71) Applicant: 3M INNOVATIVE PROPERTIES COMPANY, St. Paul, MN (US)

(72) Inventors: Vivek Bharti, Cottage Grove, MN (US); Matthew T. Scholz, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 14/721,157

(22) Filed: May 26, 2015

(65) Prior Publication Data

US 2015/0250931 A1 Sep. 10, 2015

Related U.S. Application Data

(63) Continuation of application No. 12/936,255, filed as application No. PCT/US2009/039058 on Apr. 1, 2009, now abandoned.
(Continued)

(51) Int. Cl.
*A61M 1/00* (2006.01)
*A61M 27/00* (2006.01)
(Continued)

(52) U.S. Cl.
CPC ....... *A61M 1/0049* (2013.01); *A61F 13/0216* (2013.01); *A61F 13/0226* (2013.01); *A61M 1/009* (2014.02); *A61M 1/0088* (2013.01); *A61M 27/00* (2013.01); *A61F 13/00068* (2013.01); *A61F 2013/0054* (2013.01); *A61F 2013/00536* (2013.01); *A61M 1/0023* (2013.01);
(Continued)

(58) Field of Classification Search
CPC .... A61M 1/0088; A61M 27/00; A61M 1/009; A61M 1/0049; A61F 13/02; A61F 13/0216
USPC .................. 604/319, 289, 304, 305
See application file for complete search history.

(56) References Cited

U.S. PATENT DOCUMENTS

RE24,906 E 12/1960 Ulrich
3,389,827 A 6/1968 Abere et al.
(Continued)

FOREIGN PATENT DOCUMENTS

CN 1583541 2/2005
EP 0 051 935 B1 11/1986
(Continued)

OTHER PUBLICATIONS

PCT International Search Report.
(Continued)

*Primary Examiner* — Andrew J Mensh
(74) *Attorney, Agent, or Firm* — 3M Innovative Properties Company; Trisha D. Adamson

(57) ABSTRACT

A composite wound dressing apparatus promotes healing of a wound via the use of a micropump system. The micropump system includes a micropump that applies a subatmospheric pressure to the wound to effectively draw wound fluid or exudate away from the wound bed, or deliver fluids to the wound bed, without the need for a cumbersome external pressure (e.g. vacuum) source. Hence, the wound dressing and micropump system is portable which allows the patient mobility that is unavailable when an external vacuum source is used.

16 Claims, 14 Drawing Sheets

Related U.S. Application Data

(60) Provisional application No. 61/042,698, filed on Apr. 4, 2008.

(51) Int. Cl.
*A61F 13/02* (2006.01)
*A61F 13/00* (2006.01)
*A61M 35/00* (2006.01)

(52) U.S. Cl.
CPC ......... *A61M 1/0031* (2013.01); *A61M 1/0066* (2013.01)

(56) References Cited

U.S. PATENT DOCUMENTS

| | | |
|---|---|---|
| 3,645,835 A | 2/1972 | Hodgson |
| 4,112,213 A | 9/1978 | Waldman |
| 4,310,509 A | 1/1982 | Berglund et al. |
| 4,323,557 A | 4/1982 | Rosso et al. |
| 4,398,910 A | 8/1983 | Blake et al. |
| 4,472,480 A | 9/1984 | Olson |
| 4,485,809 A | 12/1984 | Dellas |
| 4,541,426 A * | 9/1985 | Webster ............ A61F 13/00034 602/42 |
| 4,569,674 A | 2/1986 | Phillips et al. |
| 4,595,001 A | 6/1986 | Potter et al. |
| 4,598,004 A | 7/1986 | Heinecke |
| 4,600,001 A | 7/1986 | Gilman |
| 4,627,138 A | 12/1986 | Im |
| 4,655,754 A | 4/1987 | Richmond et al. |
| 4,737,410 A | 4/1988 | Kantner |
| 4,826,494 A | 5/1989 | Richmond et al. |
| 4,969,880 A | 11/1990 | Zamierowski |
| 5,088,483 A | 2/1992 | Heinecke |
| 5,100,396 A | 3/1992 | Zamierowski |
| 5,153,859 A | 10/1992 | Chatigny et al. |
| 5,160,315 A | 11/1992 | Heinecke et al. |
| 5,261,893 A | 11/1993 | Zamierowski |
| 5,527,293 A | 6/1996 | Zamierowski |
| 5,549,584 A | 8/1996 | Gross |
| 5,636,643 A | 6/1997 | Argenta et al. |
| 5,645,081 A * | 7/1997 | Argenta ................. A61B 90/00 128/897 |
| 5,738,642 A | 4/1998 | Heinecke et al. |
| 5,783,120 A | 7/1998 | Ouderkirk et al. |
| 5,803,086 A | 9/1998 | Scholz et al. |
| 5,825,543 A | 10/1998 | Ouderkirk et al. |
| 5,961,298 A * | 10/1999 | Bar-Cohen ............ F04B 19/006 417/322 |
| 5,977,585 A | 11/1999 | Vasché |
| 5,977,685 A | 11/1999 | Kurita et al. |
| 5,979,450 A | 11/1999 | Baker et al. |
| 5,997,800 A | 12/1999 | Wimberger Friedl et al. |
| 5,997,880 A | 12/1999 | Calendra et al. |
| 6,169,224 B1 | 1/2001 | Carlos et al. |
| 6,305,907 B1 * | 10/2001 | Becker .................. A61L 2/07 417/53 |
| 6,343,129 B1 | 1/2002 | Pelrine et al. |
| 6,420,622 B1 | 7/2002 | Johnston et al. |
| 6,566,575 B1 * | 5/2003 | Stickels ............... A61F 13/023 602/41 |
| 6,605,246 B2 | 8/2003 | Zhang et al. |
| 6,685,682 B1 | 2/2004 | Heinecke et al. |
| 6,742,522 B1 | 6/2004 | Baker et al. |
| D493,230 S | 7/2004 | Liedtke et al. |
| 6,867,342 B2 | 3/2005 | Johnston et al. |
| 6,893,655 B2 | 5/2005 | Flanigan et al. |
| 6,949,283 B2 | 9/2005 | Kollaja et al. |
| 6,994,904 B2 | 2/2006 | Joseph et al. |
| 7,005,143 B2 | 2/2006 | Abuelyaman et al. |
| 7,179,245 B2 | 2/2007 | Giori |
| 7,214,217 B2 | 5/2007 | Pedersen et al. |
| 7,216,651 B2 | 5/2007 | Argenta et al. |
| 7,270,860 B2 | 9/2007 | Giori |
| 7,569,742 B2 | 8/2009 | Haggstrom et al. |
| 7,777,397 B2 | 8/2010 | Bharti |
| 7,838,717 B2 | 11/2010 | Haggstrom et al. |
| 2002/0082540 A1 | 6/2002 | Johnson et al. |
| 2003/0097100 A1 | 5/2003 | Watson |
| 2003/0152463 A1 * | 8/2003 | Shuler ................. F04B 43/043 417/53 |
| 2004/0073151 A1 | 4/2004 | Weston |
| 2004/0234401 A1 | 11/2004 | Banister |
| 2005/0045210 A1 | 3/2005 | Baugh |
| 2005/0089539 A1 | 4/2005 | Scholz et al. |
| 2006/0051384 A1 | 3/2006 | Scholz et al. |
| 2006/0051385 A1 | 3/2006 | Scholz |
| 2006/0052452 A1 | 3/2006 | Scholz |
| 2007/0055209 A1 * | 3/2007 | Patel ................. A61F 13/00063 604/315 |
| 2007/0073151 A1 | 3/2007 | Lee |
| 2007/0078366 A1 | 4/2007 | Haggstrom et al. |
| 2007/0156075 A1 | 7/2007 | Heinecke |
| 2007/0172157 A1 | 7/2007 | Buchman |
| 2007/0209326 A1 | 9/2007 | Tretina |
| 2007/0219512 A1 | 9/2007 | Heaton et al. |
| 2007/0292055 A1 | 12/2007 | Reuhs et al. |
| 2010/0286639 A1 | 11/2010 | Scholz |
| 2011/0106030 A1 | 5/2011 | Scholz |

FOREIGN PATENT DOCUMENTS

| | | | |
|---|---|---|---|
| JP | 4-15832 | 1/1992 | |
| WO | WO 93/09727 A1 | 5/1993 | |
| WO | WO 02/096647 A1 | 12/2002 | |
| WO | WO 2005/042974 A1 | 5/2005 | |
| WO | WO 2006/065884 A2 | 6/2006 | |
| WO | WO 2007/030601 A2 | 3/2007 | |
| WO | WO 2007030601 A2 * | 3/2007 | ......... A61F 13/0203 |
| WO | WO 2008/019310 A1 | 2/2008 | |

OTHER PUBLICATIONS

Written Opinion of the International Searching Authority.
Pope, et al., Dielectric Elastomer Laminates for Active Membrane Pump Applications, Proc. of SPIE, 2004, pp. 60-67, vol. 5385.
Ervin, James D., Recurve Piezoelectric-Strain-Amplifying Actuator Architecture, IEEE/ASME Transactions on Mechatronics, Dec. 1998, vol. 3, No. 4.
Nostrand-Reinhold, Van, Handbook of Pressure Sensitive Adhesive Technology, 1982, pp. 384-403, Chapter 18.

* cited by examiner

WOUND DRESSING WITH MICROPUMP

CROSS REFERENCE TO RELATED APPLICATIONS

This application is a continuation of U.S. patent application Ser. No. 12/936,255, filed Jan. 5, 2011, which is a national stage filing under 35 U.S.C. 371 of PCT/US2009/039058, filed Apr. 1, 2009, which claims priority to U.S. Provisional Application No. 61/042,698, filed Apr. 4, 2008, the disclosure of which is incorporated by reference in their entirety herein.

FIELD OF THE INVENTION

The present disclosure relates to an apparatus for treating an open wound, and, more specifically, relates to a wound dressing with a micropump adapted for both introducing fluids into and evacuating fluids from a wound to facilitate the wound healing process.

BACKGROUND

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close naturally. Such wounds have presented difficulties to medical personnel for many years.

For example, skin ulcers are a common problem among many diabetics, and are often brought on by poor blood circulation and nerve damage associated with diabetes and/or vascular disease. The treatment of such ulcers often involves grafting skin from a relatively healthy donor site to an ulcerous wound site. Split thickness surgical skin graft techniques may be employed to obtain skin grafts from donor sites that can then heal spontaneously. Full thickness skin grafts, on the other hand, generally require closure of the donor site. Furthermore, many wounds can become stalled in a "chronic condition" in which further healing does not occur and, in fact, wound may actually increase in size and depth.

Wound dressings have been used in the medical industry to protect and/or facilitate healing of open wounds. Although various types of dressing materials have been successfully employed, membranes comprising semi-permeable materials are often preferred because they can increase patient comfort and lower the risk of infection. Semi-permeable membranes generally pass moisture vapors, but are generally impervious to liquids. Thus, they can promote healing by permitting a wound site to "breathe". An industry standard is Tegaderm™ sold by 3M Company, St. Paul, Minn. Although transparent dressings can "breathe", they often do not have sufficient moisture vapor transmission rates (MVTR) to allow evaporation of excess wound fluid exudate. If allowed to accumulate and/or remain over the wound optimal wound healing will not occur.

In surgical wounds this is alleviated by using a wound drain that removes excess fluid to a remote container using an applied vacuum (reduced pressure). Use of wound drains often uses a separate incision to introduce the drain. Many wound dressings for chronic wounds absorb excess wound fluid. Examples include hydrocolloid adhesive dressings, absorbent foam dressings, alginate dressings, hydrogel dressings and the like. While these dressings absorb excess wound fluid they can become saturated and allow wound fluid to build up in highly exuding wounds. Further they will not optimize the wound healing environment for wounds that tend to remain dry. These dry wounds may be characterized by insufficient blood flow to the wound bed.

Another technique has been to use negative pressure therapy, which is also known as suction or vacuum therapy. These devices apply a vacuum to a wound bed beneath a film dressing. In addition to removing excess wound fluid, the vacuum is believed to allow flow of interstitial fluid into the wound bed to promote healing. Commercial devices are sold by KCI under the "Wound Vac" trademark and by Smith and Nephew (formerly Bluesky Medical) under the tradename "VISTA". These devices comprise a motorized electric vacuum pump, wound dressing and a wound fluid trap. The wound pumps are reusable so to minimize contamination of other patients a fluid trap is placed between the vacuum pump and the wound dressing. Thus, when the trap is filled the therapy must be interrupted to change the trap. Finally, since the entire system operates at reduced pressure it becomes difficult, if not impossible, to remove a wound fluid sample for analysis without interrupting therapy. These systems are generally large and may not be easily portable.

Smaller systems have been suggested such as in U.S. Patent Application Publication No. 2007/0078366 A1 which discloses a composite wound dressing apparatus consisting of a multilayer wound dressing and a micropump. The wound dressing is described as having a base layer, a packing layer, an absorbent layer, and a top sheet. The top sheet is said to be sealed to seal the wound dressing (paragraph 0032). Paragraph 0034 states that "The micropump 120 may be embedded within the absorbent layer 106 or mounted to the layer 106, or alternatively associated within the confines of the wound dressing 100." Thus, during operation the micropump is sealed within the cavity formed by the wound dressing and the wound, as illustrated in FIGS. 1, 2, 4 and 6 of U.S. Patent Application Publication No. 2007/0078366. The micropump is said to pull a vacuum on the wound bed (see e.g. paragraph 0034). This appears fundamentally impossible with the arrangement disclosed. Because the micropump is located within a sealed cavity having no exit from the dressing, a vacuum cannot be generated without exhausting fluid (air or liquid) from the wound cavity. As described and illustrated the inlet and outlet of the micropump are both within the wound cavity compartment.

A further problem with the composite dressing design disclosed in U.S. Patent Application Publication No. 2007/0078366 is that many (or perhaps most) wounds that require vacuum therapy can generate large volumes of fluid. The disclosure provides that removal of fluid from the dressing occurs by opening an access door (see paragraph 0033) and removing the saturated absorbent layer. For many wounds this could require frequent changes which is inconvenient, unnecessarily exposes the healthcare worker to body fluids, and requires significantly more labor than current systems which collect the exudate into a canister.

Ease of use, efficiency of healing a wound, and a source of constant negative pressure are ongoing issues that need to be addressed by continuing improvements in wound therapy.

SUMMARY OF THE INVENTION

The wound dressing micropump system of the present invention comprises a wound dressing, micropump, and fluid accumulation device. The wound dressing comprises an adhesive coated optionally, a thin film dressing optionally with a valve or other micropump attachment means. The micropump is placed between the dressing and the fluid accumulation device such that the fluid enters the inlet side of the micropump from the wound dressing and exits to the fluid accumulation device under positive pressure. In a preferred embodiment the micropump is integral with the dressing and driven by a small battery power source. The fluid accumulation device may be as simple as a bag or canister, can optionally incorporate fluid absorbents such as supersorbents, and may optionally comprise a vent.

In one preferred embodiment, a wound dressing apparatus includes a wound dressing dimensioned for positioning relative to a wound bed and a micropump system. The micropump system includes a micropump for applying subatmospheric pressure to at least the wound dressing to facilitate removal of fluid from the wound bed and promote the flow of interstitial fluid into the wound bed. The micropump is preferably mounted on the wound dressing such that it is integral with the wound dressing. In another preferred embodiment the micropump is in fluid communication with the wound dressing. The preferred micropump is adapted to produce subatmospheric pressure ranging from about 5 mmHg to about 500 mmHg and preferably ranging from about 25 mmHg to about 250 mmHg below atmospheric pressure.

Preferred micropumps operate without an electric motor (i.e. do not have a rotor). The preferred micropumps utilize elastomeric diaphragms to move air and wound fluid. As used herein a "micropump" means a micropump with an actuator dimension of less than about 20 cm$^2$, preferably less than 10 cm$^2$, and most preferably less than about 8 cm$^2$. In the case of micropumps with multiple actuators the actuator dimension area is calculated in total.

In a preferred embodiment, the micropump is low cost and disposable which can reduce infection transmission. Furthermore, the preferred micropump dressing system can remove fluid from the wound using a reduced pressure (less than atmospheric pressure, i.e. a vacuum) but can also micropump the fluid to an accumulation device under positive pressure (greater than atmospheric pressure).

The present invention discloses a wound micropump made by using an elecroactive (such as a Piezoelectric or electrostrictive) diaphragm. The diaphragm is preferably constructed at least in part from an electroactive film that provides mechanical deformation in response to applied electric field, and thus serves as an actuator.

Unlike other types of wound vacuum systems, the configuration of the system disclosed eliminates the use of "fluid traps" which can become filled and thus contaminate the reusable motorized micropumps associated therewith. Such systems also must be shut down in order to drain the trap. The positive pressure wound fluid accumulation devices of the present invention may be replaced without interrupting the wound therapy. Finally, the micropump dressing systems are significantly smaller than prior art negative pressure therapy devices, less complicated, and quiet. This allows for greater patient comfort and easy ambulation for those patients that are capable.

The preferred wound dressing includes a backing layer with an interior portion surrounded by a perimeter. The backing includes a skin contact surface with an adhesive coating. The adhesive coating may be applied to all or a portion of the wound dressing but is at least applied to the skin contact perimeter. The adhesive may or may not be applied over the interior wound contact portion. The backing layer is further described below, and preferably comprises a breathable semi-permeable material film that is able to pass moisture vapors but is generally imperviousness to liquids to prevent bacterial contamination and to ensure an adequate vacuum can be applied to the treatment area. The adhesive coating should likewise be semi-permeable and may be a continuous or discontinuous pattern. Discontinuous patterns may be printed or coated engineered designs or may be random patterns. Discontinuous random patterns may be created for example, by using a blown microfiber (BMF) pressure sensitive adhesive. Although the preferred embodiments use an adhesive to form a seal, dressings are also contemplated that do not have an adhesive coating and seal over the wound, such as a circumferential wrap around a limb or abdomen.

The wound dressing may optionally include at least one of a number of actives including for example, medicaments, anti-infective agents, antimicrobials, antiseptics (for example polyhexamethylene biguanide (hereinafter, "PHMB"), chlorhexidine, silver, iodine, an iodophor, benzalkonium chloride, hydrogen peroxide as well as the antiseptics disclosed in the following U.S. Patent Application Publication Nos: US 2005/0089539, US2006/0051385, US2006/0052452, and US2006/0051384 which are incorporated herein by reference), antibiotics, analgesics, local anesthetics, anti-inflammatory agents, healing factors, vitamins, growth factors, enzyme inhibitors such as matrix metalloproteinase (MMP) inhibitors, and nutrients and/or one of a microbead packing and/or absorbent foam. Such actives may be introduced by elution off of any portion of the wound dressing including the backing, adhesive or porous filter, or from a separate storage chamber that allows controlled introduction of the medication into the wound space due to the reduced pressure environment. Alternatively, medication may be introduced as taught in U.S. Pat. No. 6,867,342 or by injecting the medication directly through the dressing.

A wound dressing may also comprise a porous filter component which serves to filter out large debris that may clog the micropump. In one embodiment the porous filter comprises an intermediate layer of wound packing material placed between a wound site and the cover dressing. The intermediate layer can comprise a variety of wound packing materials with varying properties such as absorbency, wicking or capillary action, and surface contact action. The intermediate material layer is primarily located in a chamber formed between the wound (treatment area) and the dressing.

For the following defined terms, these definitions shall be applied, unless a different definition is given in the claims or elsewhere in the specification.

The term "electrically responsive" refers to an element which may store, develop or accept an electrical charge. These elements typically comprise alternating layers of conductive and nonconductive materials.

The term "cutting plane" (i.e., cutting location) refers to an imaginary plane in relation to a three-dimensional object. For example, a cutting plane oriented in a y-z plane is useful for separating individual electrically responsive elements. The cutting plane or cutting location is perpendicular to the x-dimension of the article for dividing the elements, where faces of the alternating conductive regions of the conductive layer are exposed and coincident to one of the two faces of the element after separation.

The term "unit cell" refers to the element which repeats or extends along a dimension being divisible. For example, a unit cell for an electrically responsive element comprises at least one nonconductive layer and at least two conductive layers. The nonconductive layer is located in between the conductive layers. The unit cell is separable from a plurality of unit cells extending in the x-dimension at a y-z cutting plane.

The term "interstices" refers to a space between things or parts. For example, the interstices between the conductive regions of the conductive layer refer to the space between the regions extending in the x-dimension. The interstices of an electrically responsive element may contain polymeric nonconductive material. The interstices may also be referred to as nonconductive regions.

The term "reference plane" refers to an imaginary plane in relation to a three-dimensional object. For example, a reference plane oriented in a y-z plane is coincident and parallel to the surface of the conductive regions of the conductive layer, or to a face of an article or electrically responsive element. The reference plane is perpendicular to the x-dimension and parallel to the cutting plane(s). The reference plane may also be a cutting plane.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

BRIEF DESCRIPTION OF THE DRAWINGS

Various embodiments of the subject wound dressing are described herein with reference to the drawings wherein.

DESCRIPTION OF THE PREFERRED EMBODIMENTS

Figure 1:
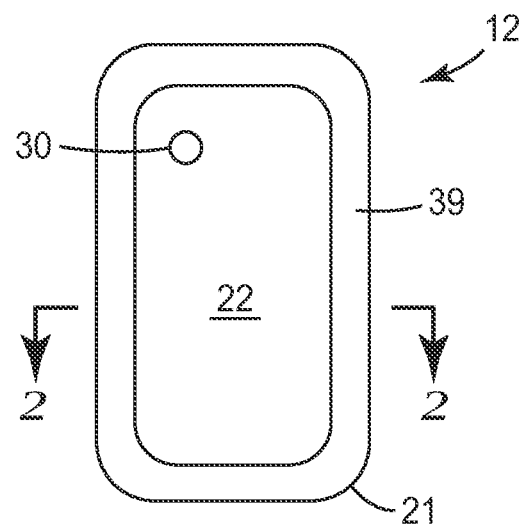
FIG. 1 is a plan view of one embodiment of a wound dressing according to the present invention.

In the following description of preferred embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The composite wound dressing apparatus of the present disclosure promotes healing of a wound via the use of a micropump system. Fluid removed from the wound dressing may include gases and/or liquids (which may contain dispersed solid particles such as necrotic tissue, blood clots, etc.). The fluid removal can be performed without removing or otherwise disturbing the medical dressing. Without limitation on the generality of the useful applications of the present invention, the dressing may be applied over surgical wounds, cosmetic surgical procedures, burns, cuts, scrapes and ulcers of various types, e.g. diabetic, decubitus, peripheral vascular disease, venous stasis and trauma ulcers.

As used herein, the term "sealed environment" means that fluids (and solids) from the ambient atmosphere surrounding the exterior of a medical dressing attached over a wound cannot freely enter the sealed environment. The sealed environment preferably includes a hermetic seal between the medical dressing and the surface surrounding the wound such that a negative pressure can be maintained in the sealed environment. It may, for example, be preferred that the medical dressing be capable of holding (at least temporarily as described herein) a vacuum of 100 mmHg (i.e., a pressure that is 100 mmHg below atmospheric pressure) and perhaps a vacuum as much as 200 mmHg Although some conventional medical dressings can provide such a sealed environment, the medical dressings of the present invention can do so while also offering the opportunity to remove fluids (liquids and/or gases) into and out of the sealed environment through at least one opening provided as a part of the medical dressing.

Fluid removal from the sealed environment may be useful to provide negative or reduced pressure therapies to a wound over which the medical dressing is located. In a preferred embodiment, the sealed environment created by a medical dressing of the present invention may preferably be maintained at a negative pressure (i.e., pressure below the ambient atmospheric pressure) in the absence of active vacuum source in fluid communication with the sealed environment. In other words, the medical dressings of the present invention may be used to maintain a sealed environment with a negative or reduced pressure in the periods between active removal of fluids from the sealed environment. As a result, the medical dressings can provide a negative or reduced pressure environment with only intermittent or periodic fluid removal.

Although the magnitude of the negative pressure maintained in the sealed environment by the medical dressings will typically deteriorate over time (after reaching a maximum during that active removal of fluids from the sealed environment), it may be preferred that the medical dressing be capable of maintaining the negative pressure for at least some significant period of time. In some embodiments, it may be preferred that the medical dressing be capable of maintaining at least some level of negative pressure in the sealed environment (in the absence of active fluid removal) for a period of 1 minute or more, 5 minutes or more, 10 minutes or more, 15 minutes or more, 30 minutes or more, or even 60 minutes or more.

Deterioration of the negative pressure within the sealed environment defined by the medical dressing may be caused by a variety of sources. For example, some of the deterioration may be due to the diffusion of gas into the sealed environment through the backing of the medical dressing and/or the adhesive attaching the medical dressing to a subject. Another source of negative pressure deterioration in the sealed environment may be caused by gases and/or liquids entering the sealed environment from the subject (i.e., through the wound itself and/or the tissue surrounding the wound).

Although the medical dressings of the present invention may be used to provide negative pressure wound therapy, in some instances fluids or other materials may potentially be delivered into the sealed environment through the medical dressing by the micropump. It may be preferred that the delivery of materials into the sealed environment through the medical dressing by the micropump does not functionally compromise the ability of the medical dressing to define a sealed environment as described herein.

To retain a negative pressure within the sealed environments, it may be preferred that the openings in the medical dressings be one-way valves. In other words, it may be preferred that the valve allows fluid flow in one direction (out of the sealed environment) and restricts or prevents flow in the opposite direction (into the sealed environment). Alternatively, the valve allows fluid flow in one direction (into the sealed environment) and restricts or prevents flow in the opposite direction (out of the sealed environment).

In various embodiments, the medical dressings may include stand-off elements to provide open fluid pathways to the valves (that resist closing under negative pressure in the sealed environment), barrier elements (to limit clogging of the valves); septum elements, and/or closure elements. The closure elements may, in some instances, be provided over the valves, such that the valves are sealed shut until the closure elements are removed.

Figure 2:
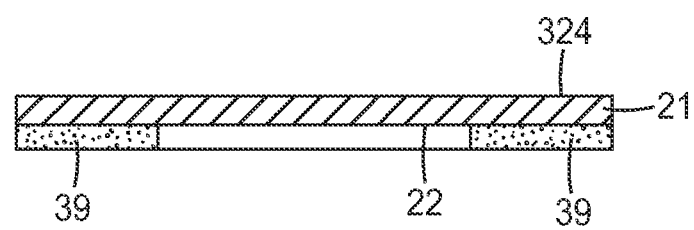
FIG. 2 is a cross-sectional view of the wound dressing of FIG. 1 taken along line 2-2 in FIG. 1.
Figure 3:
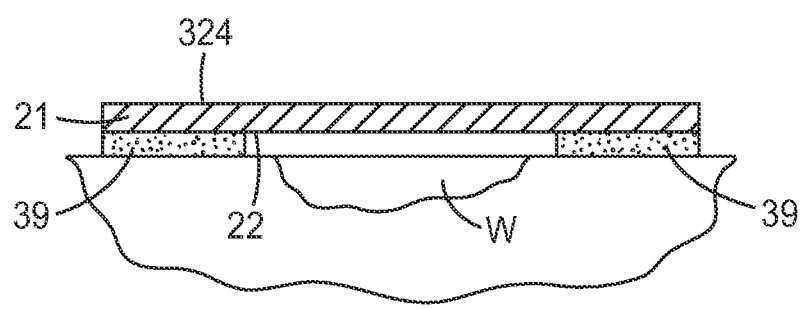
FIG. 3 is a cross-sectional view of the wound dressing of FIGS. 1 and 2 located over a wound W.

One exemplary embodiment of a wound dressing according to the present invention is depicted in FIGS. 1, 2, and 3. The wound dressing 12 includes a backing 21 (which may preferably be conformable as described herein). The backing 21 includes two opposed major surfaces: an interior surface 22 and an external surface 324. In use, the interior surface 22 faces a wound (or other body site) over which the dressing is placed while the external surface 324 faces away from the wound (or other body site).

Potentially suitable materials for the wound backing 21 are described in more detail below, but functionally, the backing 21 is preferably made of materials that serve as a barrier to both liquid and rapid gas diffusion. The barrier properties of the backing 21 may or may not be absolute, e.g., the backing 21 may allow for limited passage of gas, although the backing 21 (and the other components of the dressing 12) preferably provide sufficient barrier properties to the passage of gas such that, when placed over a wound, an adequate vacuum environment can be at least temporarily applied to the treatment area. For example, the backings may preferably have relatively high moisture vapor transmission rates, but be substantially impervious to liquids.

The dressing also includes an adhesive on the interior surface of the backing layer such that the dressing can be adhered to a subject over a wound with the interior surface facing a wound. The adhesive 39 may cover all or part of the interior surface 22 in a continuous and/or pattern coated fashion. The adhesive 39 as depicted in FIG. 2 is provided only around the perimeter or border of the backing 21 such that the adhesive 39 forms a frame around a central part of the interior surface 22 of the backing 21. Many other arrangements are possible. One arrangement is depicted in FIG. 3 in which the dressing 12 is located over a wound W while the adhesive 39 is attached to the tissue (e.g., skin) surrounding the wound W. The dressing 12, along with the wound W and the tissue surrounding the wound, preferably define a sealed environment in which the wound W is isolated from the surrounding environment. The interior surface 22 of the backing 21 faces the sealed environment in which the wound is located while the external surface 324 of the backing 21 faces away from the wound W.

The adhesive 39 as depicted in FIGS. 1 and 2 may preferably be exposed on only a portion of the interior surface 22 of the backing 21. In the embodiment depicted in FIGS. 1 and 2, the adhesive 39 is provided on only a portion of the interior surface 22 (i.e., the central portion of the interior surface 22 is free of the adhesive 39). In other embodiments, however, adhesive may be provided over substantially all of the interior surface 22 with a portion of the adhesive covered by another element such that only a portion of the adhesive remains exposed for attachment to a subject.

In any embodiment, however, it may be preferred that the adhesive 39 extend continuously around the entire perimeter of the backing 21 such that the dressing 12, when attached to a subject, can form a sealed environment over a wound, with the bounds of the sealed environment being defined by the interior surface 22 of the backing 21 as adhered to the subject over a wound by the adhesive 39.

In preferred embodiments the dressings are adapted for easy deliver to the wound. This may be done, for example, using handles and optionally a stiffening strip as disclosed in U.S. Pat. Nos. 6,742,522 and 5,979,450 incorporated herein by reference or by using a so called "frame delivery" as disclosed in U.S. Pat. Nos. 6,169,224, 5,088,483, and 4,598,004 also incorporated herein by reference.

The adhesive is typically protected by a liner. Liners that are suitable for use in the adhesive composites of the present invention can be made of kraft papers, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference, describes low surface energy perfluorochemical liners. The preferred liners are papers, polyolefin films, or polyester films coated with silicone release materials. Examples of commercially available silicone coated release papers are POLYSLIK™ silicone release papers available from James River Co., H. P. Smith Division (Bedford Park, Ill.) and silicone release papers supplied by Daubert Chemical Co. (Dixon, Ill.). The most preferred liner is 1-60BKG-157 paper liner available from Daubert, which is a super calendared Kraft paper with a water-based silicone release surface. Alternatively the wound dressing may be linerless and delivered in roll form such as described in U.S. Pat. No. 5,803,086.

The wound dressing is preferably a single piece but may be formed from two or more pieces that come together to form seams as taught in U.S. Pat. No. 4,969,880 incorporated herein by reference.

In some embodiments, it may be preferred that the medical dressing include absorbent material such as a wound packaging material, to absorb fluids (e.g., liquids) entering the sealed environment. Examples of potentially suitable absorbent materials may include, but are not limited to, hydrophilic foams, woven materials, nonwoven materials, etc. and combinations thereof. It may be preferred that the absorbent material be both absorbent and capable of releasing at least some (preferably a majority) of any absorbed fluids when a vacuum is applied to the sealed environment through a valve. By releasing absorbed fluids during the removal of fluids from the sealed environment, the ability of the absorbent material to absorb fluids may be regenerated—which may prolong the useful life of the medical dressing.

The wound dressing 12 further may include a normally-closed valve 30 that is attached to the backing 21 over one or more passages that are formed through the backing 21. The valve allows fluid to be removed from the sealed environment defined by the wound dressing. Fluid flow through the one or more passages in the backing 21 is controlled by the valve 30. The valve 30 (preferably be a one-way valve) may be connected to the micropump or be in fluid communication with the micropump. It may be preferred that the micropump include a seat that can seal against the external surface of the backing of the wound dressing to provide a fluid-tight seal. The valve may then be used to provide a vacuum environment to a wound over which the dressing 12 is placed as described herein. Although the wound dressing depicted in FIGS. 1 and 2 includes only one valve 30, wound dressings of the present invention may include more than one valve if additional access to the sealed environment defined by the dressing is desired. Exemplary valves for this purpose are more completely described in PCT Publication No. WO2005/124125 and incorporated by reference in its entirety. In some embodiments, such a valve may comprise a plurality of polymeric film layers aligned with the backing of the wound dressing, wherein the plurality of polymeric film layers comprises a flap layer comprising a flap formed therein.

Figure 22A:
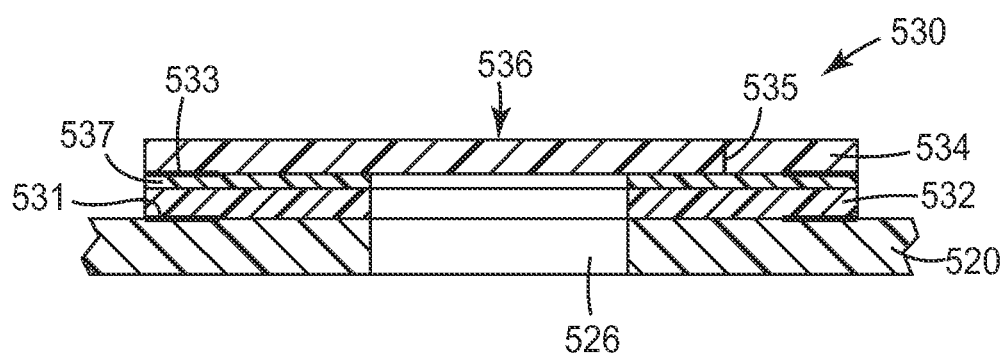
FIG. 22A is an enlarged cross-sectional view of one exemplary valve that may be used in a medical dressing of the present invention, wherein the valve is in a closed configuration.
Figure 22B:
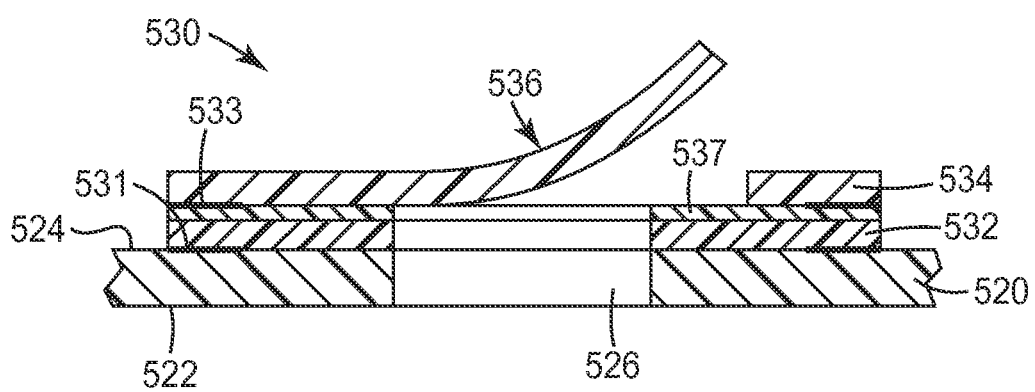
FIG. 22B is an enlarged cross-sectional view of the valve of FIG. 22A in an open configuration.
Figure 22C:
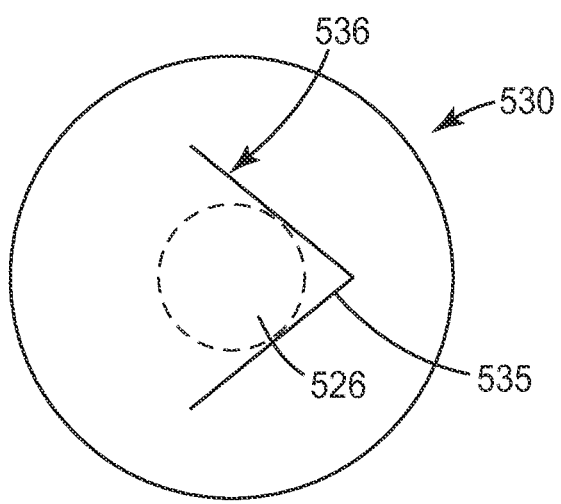
FIG. 22C is a plan view of the external surface of the valve of FIGS. 22A and 22B.

One exemplary embodiment of a valve 530 that may be used in a medical dressing as depicted in FIGS. 1-3 is found in FIGS. 22A-22C. Although this valve represents one embodiment of a potentially suitable valve that may be used in connection with the present invention, many other valves may be used in place of the specific valve structure depicted in FIGS. 22A-22C.

The valve 530 of FIGS. 22A-22C is depicted as being located over a single opening 526 formed through the backing 520, although the valve 530 may be located over two or more openings to control fluid flow through the openings. As discussed herein, the valve 530 and the opening 526 may preferably provide an evacuation port through which fluids can pass through the backing 520. The valve 530 includes a base layer 532 attached to the backing 520 and a flap layer 534 attached to the base layer 532 such that the base layer 532 is located between the flap layer 534 and the backing 520.

The base layer 532 may be attached to the backing 520 by any suitable technique or combination of techniques, e.g., adhesives, heat sealing, chemical welding, thermal welding, ultrasonic welding, etc. In the depicted embodiment, the base layer 532 is attached to the backing 520 using adhesive 531. The flap layer 534 may be attached to the base layer 532 by any suitable technique or combination of techniques, e.g., adhesives, heat sealing, chemical welding, thermal welding, ultrasonic welding, etc. In the depicted embodiment, the flap layer 534 may be attached to the base layer 532 by adhesive 533 that may preferably be located proximate the outer perimeters of the base layer 532 and the flap layer 534. The valve 530 may also include optional seating adhesive 537 on the area of the base layer 532 against which the valve flap 536 rests when in the closed position. The seating adhesive 537 may preferably have limited tack to allow opening of the valve 530 as discussed herein, but may also improve sealing of the valve 530 when in the closed configuration.

The flap layer 534 includes a slit 535 that defines the shape of a valve flap 536 in the flap layer 534. The valve flap 536 may preferably have a closed configuration in which the valve flap 536 is located over the opening 526 in the backing 520 to close the opening 526 such that fluid cannot freely pass through the opening 526 (see FIG. 22A). If present, the seating adhesive 537 may assist in sealing the valve 530. The valve flap 536 is preferably moveable to transform the valve 530 from a closed configuration to an open configuration in which fluids can pass through the opening 526 and the valve 530 (as depicted in FIG. 22B).

Transformation of the valve 530 between the open and closed configurations may preferably be performed selectively, although it may be preferred that the valve 530 be normally closed such that, in the absence of an applied force capable of opening the valve 530, the valve 530 is closed. In some embodiments, the valve 530 may be opened by a pressure differential placed across the valve 530 (i.e., across the backing from the interior surface to the external surface (i.e., interior and external surfaces 22 and 324, respectively, of the backing 21 shown in FIG. 2)). For example, the valve flap 536 may be opened when the fluid pressure on the side of the valve 530 facing in the same direction as the interior surface 522 is sufficiently larger than the forces operating on the valve flap 536 to retain it in the closed configuration. The pressure differential at which the valve 530 moves from the closed configuration to the open configuration may be referred to as the "cracking pressure".

The pressure differential across the valve 530 may be achieved by, e.g., applying the inlet of a pump (e.g., a vacuum pump) or a fluid conduit (e.g., tube, hose, etc.) leading to the inlet of a pump over the external surface of valve 530 on the external surface 524 of the backing 520. The pump is preferably capable of providing a reduced pressure environment on the external side of the valve 530 such that the pressure differential across the valve 530 (i.e., between the interior surface 522 and the external surface 524 of the backing 520) is high enough to reach the cracking pressure. Once the valve 530 is in the open configuration, fluids (gases and/or liquids) in the sealed environment defined by the dressing over the wound may be removed through the opening 526 and valve 530. The fluids removed from the sealed environment may or may not contain solid particles.

It may be preferred, but not required, that the fluid removal place the sealed environment at a negative pressure as discussed herein, although such a condition is not necessarily required. For example, the fluid removal may be limited to removing fluids such as wound exudate, blood, etc. from the sealed environment without necessarily resulting in a negative pressure condition within the sealed environment.

The valve 530 depicted in FIGS. 22A-22C is only one example of a potentially suitable valve that may be used in connection with the present invention. Some examples of other potentially suitable valves are depicted in FIGS. 23A-23C.

Figure 23A:
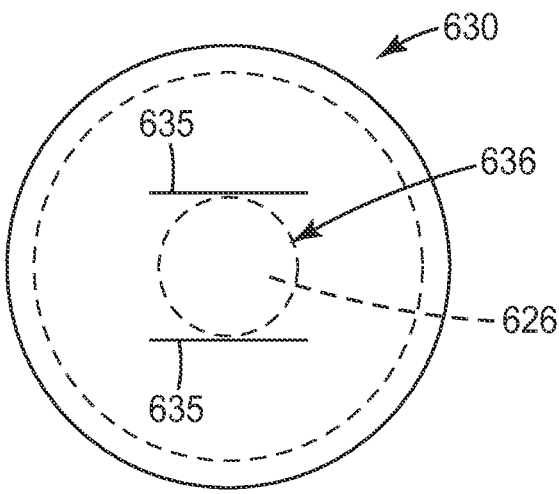
FIG. 23A is a plan view of the external surface of another exemplary valve that may be used in a medical dressing of the present invention.
Figure 23B:
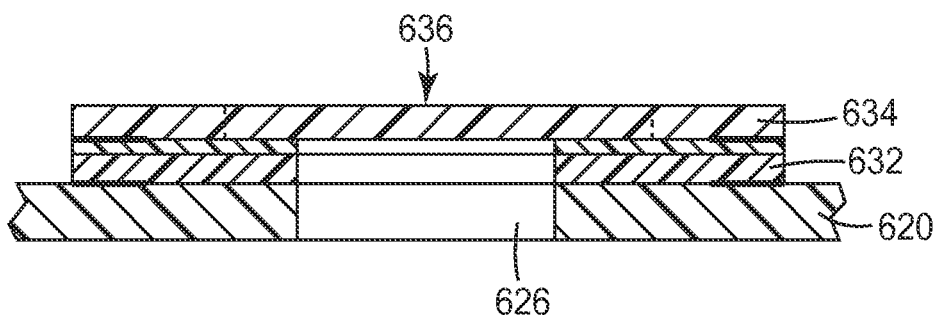
FIG. 23B is an enlarged cross-sectional view of the valve of FIG. 23A, wherein the valve is in a closed configuration.
Figure 23C:
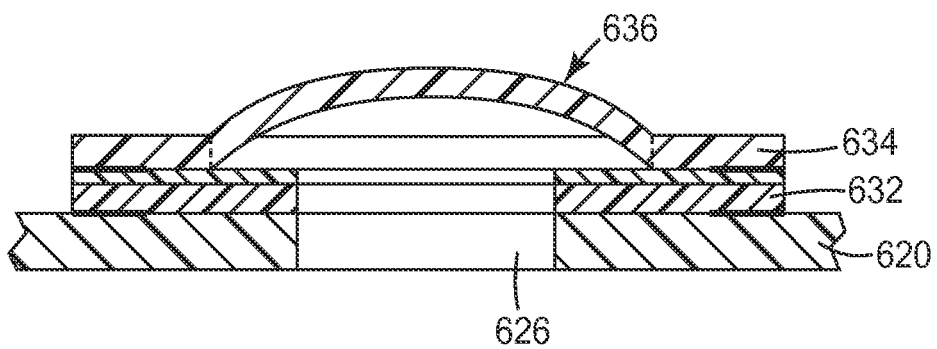
FIG. 23C is an enlarged cross-sectional view of the valve of FIG. 23A, wherein the valve is in an open configuration.

Although the valve 530 of FIGS. 22A-22C includes a valve flap 536 formed by a single continuous slit 535, the valve flaps can be formed by multiple slits as depicted in FIG. 23A. The valve 630 includes a valve flap 636 formed by slits 635 in the flap layer 634. The slits 635 preferably allow the valve flap 636 to lift away from the base layer 632 to allow fluids to pass through opening 626 in the backing 620 on which the valve 630 is located. FIG. 23B depicts the valve 630 in its closed configuration, with the valve flap 636 seated against the base layer 632, while FIG. 23C depicts the valve 630 in its open configuration with the valve flap 636 spaced from the base layer 632 such that fluids can pass through the openings formed along the slits 635.

Figure 24A:
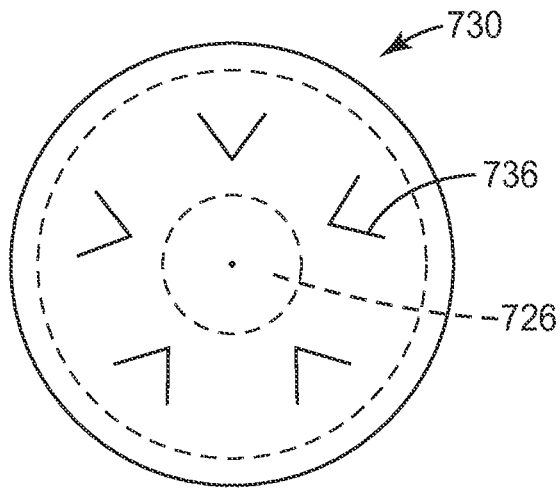
FIGS. 24A and 24B are plan views of two more exemplary valves that may be used in a medical dressing of the invention.
Figure 24B:
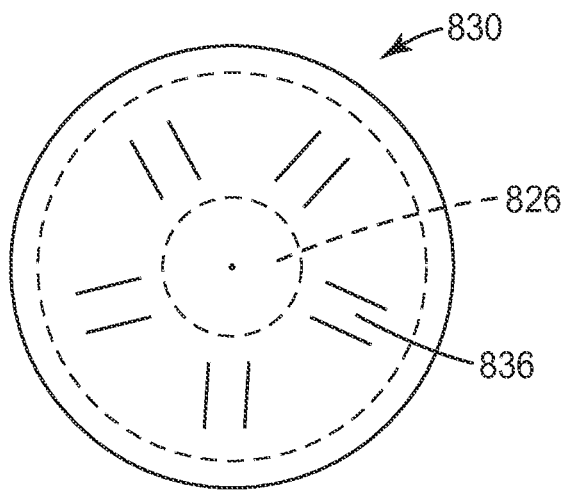

Although the valves 530 and 630 described above each include a single valve flap, the valves used in connection with the present invention may alternatively include two or more valve flaps. Examples of two potentially suitable examples are depicted in FIGS. 24A and 24B, where the valves 730 and 830 each include multiple valve flaps 736 and 836 that open to allow fluids to pass through the openings 726 and 826, respectively. Valves of the types described above in connection with FIGS. 22A-22C, 23A-23C, and 24A-24B may be characterized as being constructed of a plurality of polymeric film layers. It may further be preferred that the polymeric film layers used in such valves be flexible polymeric films. Additional features and variations, as well as a variety of methods of manufacturing valves such as those described above, may be found in U.S. Patent Application Publication No. US 2006/0228057 (Newrones et al.).

Further, many other valves can be used in place of or in addition to the valves specifically described herein. For example, valves such as those known as "Goglio" type or "Raackmann" type valves may be used in connection with the present invention. Goglio-type valves are available, for example, from Bosch, Wipf, and Wico; Raackmann-type valves are available, for example, from Amcor. Other potentially suitable valves may include duckbill or umbrella valves (examples of which are those available from Vernay Laboratories, Inc., Yellow Springs, Ohio). Still other examples of suitable vacuum valves may include those described in U.S. Pat. Nos. 6,913,803; 6,733,803; 6,607,764; and 6,539,691, each of which is incorporated herein by reference in its entirety.

As discussed herein, it may be preferred that the profile or height of the valves be limited to improve comfort, increase resistance to displacement by external forces (from, e.g., bedding, clothing, etc.).

One manner in which the low-profile valves used in connection with the medical dressings of the present invention can be characterized may be in terms of maximum thickness of the valve structure as measured normal to the major surfaces of the backing (where the major surfaces of the backing are the interior surface and the external surface). It may be preferred, for example, that the valves used in the medical dressings of the present invention have a maximum thickness of 1 centimeter (cm) or less, in some embodiments 5 millimeters (mm) or less, or even 2 mm or less, and more preferably 1 mm or less, e.g., even 200 micrometers (µm) or less.

Another manner in which the low-profile valves used in connection with the present invention can be characterized may be in the form of dead volume between the normally-closed valve and the backing. As used herein, the term "dead volume" describes the volume or space in which fluids may accumulate between the valve and the interior surface of the backing when the valve is in its normally-closed configuration. Reducing the dead volume between the normally-closed valve and the interior surface of the backing can help to reduce the profile of the valve and the dressing as a whole.

For example, the valve 530 depicted in FIGS. 22A-22C defines a dead volume that is essentially the space defined by the thickness of the backing 520 (between the interior surface 522 and the external surface 524) and the area occupied in the backing 520 by the opening 526. In this embodiment, the dead volume is further increased by the thickness of the base layer 532 because the valve flap 536 of the flap layer 534 is spaced from the external surface 524 of the backing 520 by the base layer 532.

The dead volume defined by a normally-closed valve and backing in a medical dressing of the present invention may preferably be 10 cubic millimeters ($mm^3$) or less, in some embodiments 6 mm$^3$ or less, or even 4 mm$^3$ or less, and further, in some embodiments, even 2 mm$^3$ or less, e.g. 1 mm$^3$ or less.

Preferably valve 530 is not incorporated into ports or tubing connections since these connections must be relatively rigid to prevent collapse under vacuum. These rigid structures can cause pressure points when the patient is lying on the wound, for example, when in bed.

Figure 4:
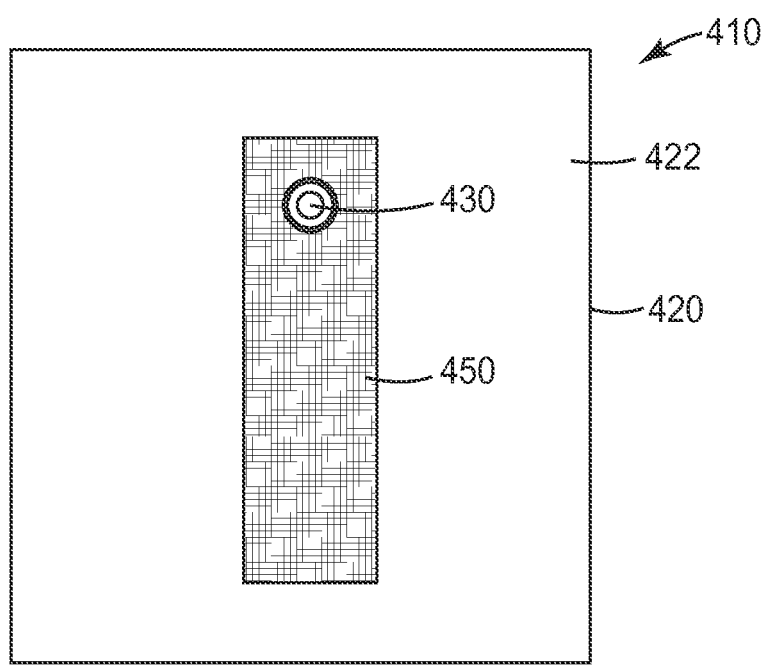
FIG. 4 is a plan view of the interior surface of an exemplary medical dressing including a stand-off element and a valve.

Another optional feature that may be included in some embodiments of the medical dressings of the present invention is a stand-off element that may be located proximate the valve on the interior surface of the backing to assist in the removal of fluids from the sealed environment. FIG. 4 is a plan view of the interior surface 422 of the backing 420 of a medical dressing 410. The medical dressing 410 may include adhesive that is exposed over the entire interior surface 422 except for the area occupied by the stand-off element 450. The adhesive may be continuous or pattern-coated, although regardless of the coating, it may be preferred that the adhesive be capable of providing a hermetic seal such that a negative pressure can be obtained in the sealed environment. One example of a potentially suitable pattern for pattern-coated adhesive may be a grid pattern. It may be preferred that the valve 430 be located within the area of the backing 420 that is occupied by the stand-off element 450, although in some embodiments, the valve 430 may be located proximate the perimeter of the stand-off element 450.

The stand-off element 450 includes some form of structure on one or more surfaces that provides open fluid pathways such that fluids within the sealed environment defined by the medical dressing 410 can be removed through the valve 430. If, for example, a stand-off element 450 is not provided and the interior surface 422 of the dressing 410 were to seal against a wound or the skin surrounding a wound, the removal of fluids from the sealed environment by the micropump could be hindered. The stand-off element 450, however, preferably is capable of maintaining open fluid pathways to facilitate fluid removal through the valve 430 even when the sealed environment is at a negative pressure relative to atmosphere, that is, the fluid pathways preferably resist collapsing—even under negative pressure.

Although the medical dressing depicted in FIG. 4 includes only one stand-off element 450 and one valve 430, the medical dressings of the present invention may include, for example, more than one valve in connection with that same stand-off element. The use of multiple valves may be beneficial if, for example, one of the valves is poorly placed relative to the sealed environment, malfunctions, becomes clogged, etc. In another variation, the medical dressings of the present invention may include more than one stand-off element, with each of the stand-off elements potentially associated with one or more valves to facilitate fluid removal from the sealed environment. The use of more than one stand-off element in connection one medical dressing may be beneficial if, for example, one of the stand-off elements is poorly placed relative to the sealed environment, becomes clogged, etc.

The stand-off elements used in the medical dressings of the present invention may take a wide variety of forms. In some embodiments, the stand-off element may be formed directly in the interior surface of the backing (by, e.g., embossing, abrading, molding, cutting, etc.). In other embodiments, the stand-off element take the form of a separate article (e.g., a film, etc.) having channels or other structures embossed, abraded, molded, cut, or otherwise formed therein. The separate article forming the stand-off element may preferably be attached to the backing by any suitable technique or combination of techniques (e.g., adhesives, heat sealing, thermal welding, etc.).

The channels in the stand-off elements may be in any pattern or shape, such as, but not limited to a honeycomb pattern of channels, grid or partial grid, series of grooves (that are, e.g., parallel, radial, etc.), posts or other discrete structures (e.g., pyramids, etc.). In some instances where the stand-off element is provided as an article that is separate from the backing of the medical dressing, the article may include fluid pathway-forming structures on both major sides of the stand-off element. Examples of some potentially suitable stand-off elements may be further described in, e.g., U.S. Patent Application Publication No. US 2007/0172157 (Buchman), U.S. Pat. No. 6,420,622 (Johnston et al.), etc.

Fluids delivered to the sealed environment through the medical dressing may include gases (e.g., oxygen, nitric oxide, ozone, etc.) and/or liquids (e.g., saline, water, etc.). Particulates may, in some instances, also be delivered to the sealed environment if, e.g., they are entrained within a fluid delivered into the sealed environment.

In some instances, it may be desirable to deliver one or more active agents to the sealed environment (and, thus, the wound covered by the dressing). The active agents may be provided as a fluid and/or may be carried within a fluid that is delivered to the internal volume. Some potentially suitable active agents may include, e.g., antimicrobials, antibiotics, analgesics, healing factors such as vitamins, growth factors, nutrients and the like. Examples of other potentially suitable agents may be described in U.S. Pat. No. 6,867,342.

If delivered, an active agent (or agents) could be supplied to the sealed environment continuously or intermittently. For example, an active agent could be delivered to the sealed environment and allowed to remain in place (i.e., resident) for a selected period of time (e.g., several hours) followed by, e.g., delivery of a second active agent, delivery of negative pressure therapy, etc. The initial active agent could be removed before delivery of the second agent or it could be allowed to remain in place. Alternatively, the sealed environment could be rinsed with, e.g., saline or another flushing solution before placing the sealed environment in a negative pressure condition, before delivery of a second agent, etc.

As discussed herein, the medical dressings of the present invention may be used for negative pressure wound therapy by providing a micropump in the medical dressing through which fluid can be removed from a sealed environment defined by the medical dressing. The fluid is removed from the sealed environment using a micropump that can preferably be attached to the medical dressing. It may be preferred that the micropump include a seat or valve that can seal against the external surface of the backing of the medical dressing to provide a fluid-tight seal.

To remove fluid from the sealed environment, the pressure surrounding the exterior of the valve can be sufficiently reduced to open the valve and remove fluid from the sealed environment through the valve. It may be preferred that the valve be a normally-closed one-way valve such that the valve recloses when the reduced pressure environment is no longer present around the exterior of the valve (i.e., the pressure differential across the valve falls below the level needed to maintain the valve in the open configuration). As discussed herein, the negative pressure can preferably be maintained within the sealed environment defined by the medical dressing.

In preferred embodiments, the wound dressing and micropump system of the present invention be capable of quickly connecting with each other to form a fluid-tight seal during removal of fluids from the sealed environments defined by the wound dressings. The wound dressing itself may preferably be featureless (e.g., present only the smooth external surface of the backing), while the pump includes a seat that provides a surface capable of sealing against the featureless backing to form the required fluid-tight seal.

In some embodiments, the wound dressings and micropump may include more conventional connections/fittings to provide a fluid-tight connection between the micropump and the wound dressings. In such an embodiment, the wound dressing kit may include a fitting that attaches to the external surface of the backing using, e.g., a pressure sensitive adhesive, etc. The fitting may, for example, include a tubing connector, Luer lock fitting, etc. designed for connection to the micropump. The adhesive used to attach the fitting to the wound dressing may be releasable, i.e., the fitting may potentially be removed from the dressing while the dressing remains in place over a wound, such that any sealed environment defined by the wound dressing remains intact during removal of the fitting.

The wound dressing micropump system includes a micropump that applies a subatmospheric pressure to the wound to effectively draw wound fluid or exudate out of the wound bed and encourage interstitial fluid to flow into the wound bed from surrounding tissues. Hence, the wound dressing apparatus in the form of wound dressing and micropump system is extremely portable which allows the patient greater mobility than is available when an external vacuum source is used. The micropump of the present invention is sufficiently small to allow even greater mobility than other semi-portable configurations wherein the patient must carry the micropump in a support bag, as is disclosed for example in U.S. Patent Application Publication No. 2007/0055209. The patient does not need to be restricted for any period of time while the wound is being treated.

In contrast to known negative pressure therapy systems, the present invention utilizes a micropump which contacts the wound fluid directly. The excess wound fluid is passed through the micropump. Thus, the micropump is preferably self priming and able to pump out air trapped between the sealed dressing and the wound bed, although manual removal of air by manipulation of the wound dressing and/or micropump is also contemplated. In operation the micropump is turned on and the air is pumped out creating a vacuum. As used herein the term "vacuum" refers to pressures less than the surrounding atmospheric pressure. Preferably the pressure is reduced by 5-250 mm mercury (Hg) (e.g. down to an absolute pressure of 500-740 mmHg but this will depend on the atmospheric pressure). When the pressure is reduced by more than 250 mmHg the patient may experience pain. Thus, preferably the pressure is not reduced by more than 200 mmHg and more preferably by not more than 175 mm Hg. Preferably, the pressure is reduced by at least 5 mmHg, 25 mmHg, more preferably at least 50 mmHg and most preferably at least 75 mm Hg in order to remove sufficient interstitial fluid.

Preferably the micropump is a low cost micropump designed to be disposable. Disposing of the micropump with each dressing change reduces the risk of bacterial contamination of the wound and transmission to other patients. Preferred micropumps are positive displacement micropumps in order to ensure they are rapid, and preferably self priming Many micropump designs are suitable including those driven by small electric motors such as micro-gear, lobe, piston, screw, peristaltic, centrifugal, and diaphragm pumps. Most preferred are the diaphragm pumps and electroresponsive micropumps as further described below that do not require a motor. These micropumps inherently have few moving parts and thus are more reliable and able to operate very quietly.

The micropumps of this invention preferably can achieve an output pressure of at least 100 mmHg above atmospheric pressure (gauge pressure). Preferably the micropumps are capable of an output pressure of at least 200 mmHg above atmospheric pressure. The micropumps should be capable of flow rates of at least about 1 ml/hr. More preferably the micropumps are capable of flow rates of at least about 3 ml/hr.

One such micropump may be made using electroactive material to form an actuator as further described below and in U.S. Pat. No. 7,777,397 and incorporated by reference in its entirety. The micropump comprises a pump chamber having an electroactive actuator on at least one face, a means of bringing fluid (gas or liquid including liquid with dispersed solids such as wound fluid) into and out of the pump chamber, a means of restricting the fluid movement outward when the chamber is filling and a means of restricting the fluid movement inward when the chamber is emptying, and a means of supplying power to the electroactive actuator at the proper voltage, frequency and amperage.

In one embodiment, the micropump comprises at least three elements: an electroresponsive element, a pair of electrodes capable of applying a voltage potential across the thickness of at least a portion of the electroresponseive element, and a power supply capable of applying the appropriate voltage drop to attain the required compression. Preferably the power (voltage drop) may be adjustable to apply intermittent or variable pressure for example by incorporation of a potentiometer. The electroresponsive element is preferably capable of achieving 0.01% strain, preferably 0.1% strain, more preferably 1% strain, even more preferably 3% strain and most preferably greater than 5% strain when a voltage is applied. The most preferred electroresponsive elements are electroactive polymers such as elastomers (polyurethanes, silicone rubber, Zetpole, VHB), visco-elastic polymers, and copolymers or terpolymers (PVDF, PVDF-TrFE, PVDF-HFP, PVDF-TrFE-HFP etc.) as further described below. The electroresponsive element also may be polymer composite film such as polymer-ceramics wherein the ceramic element may be PZT, PZN-PT, Polymer-carbon nanotubes, carbon fibers, Polyamide-PZT fibers etc.

The electroactive material can be multilayer film as disclosed in U.S. Pat. No. 7,777,397 and incorporated by reference in its entirety. The multilayer film construction helps to significantly reduce the driving voltage and better control of driving force. In this multilayer construction, the voltage is applied to the individual layers, resulting their collective movement. Reducing actuator film thickness can reduce the driving voltage significantly. In this multilayer construction, the stiffness of the diaphragm can be easily controlled by the numbers of layers while keeping the same driving voltage.

Alterntatively, or in addition to the electroactive polymers described herein, the electroresponsive element can be a magnetorestrictive material. A magnetorestrictive material as used herein is one that changes dimension by application of a magnetic field. A preferred magnetorestrictive material is Terfenol-D. For example, suitable magnetorestrictive materials may be Ferromagnetic Shape Memory Alloy Materials (FSMA) that exhibit a twinning mechanism similar to that observed in traditional shape memory alloy materials such as NiTi and CuZn. In the FSMA the shape change may be initiated using an applied magnetic field. Another material investigated is an iron/gallium alloy termed Galfenol at the Naval Surface Warfare Center (Clark et al.). See Clark, A. E., "Magnetostrictive rare earth-Fez Compounds," in *Ferromagnetic Materials: A Handbook on the Properties of Magnetically Ordered Substances* Vol. 1, Wolfarth, E. P., ed., 531-589, 1980. In these applications, a current, rather than voltage, may be used to drive the displacement of the actuator comprising magnetorestrictive materials.

Figure 5:
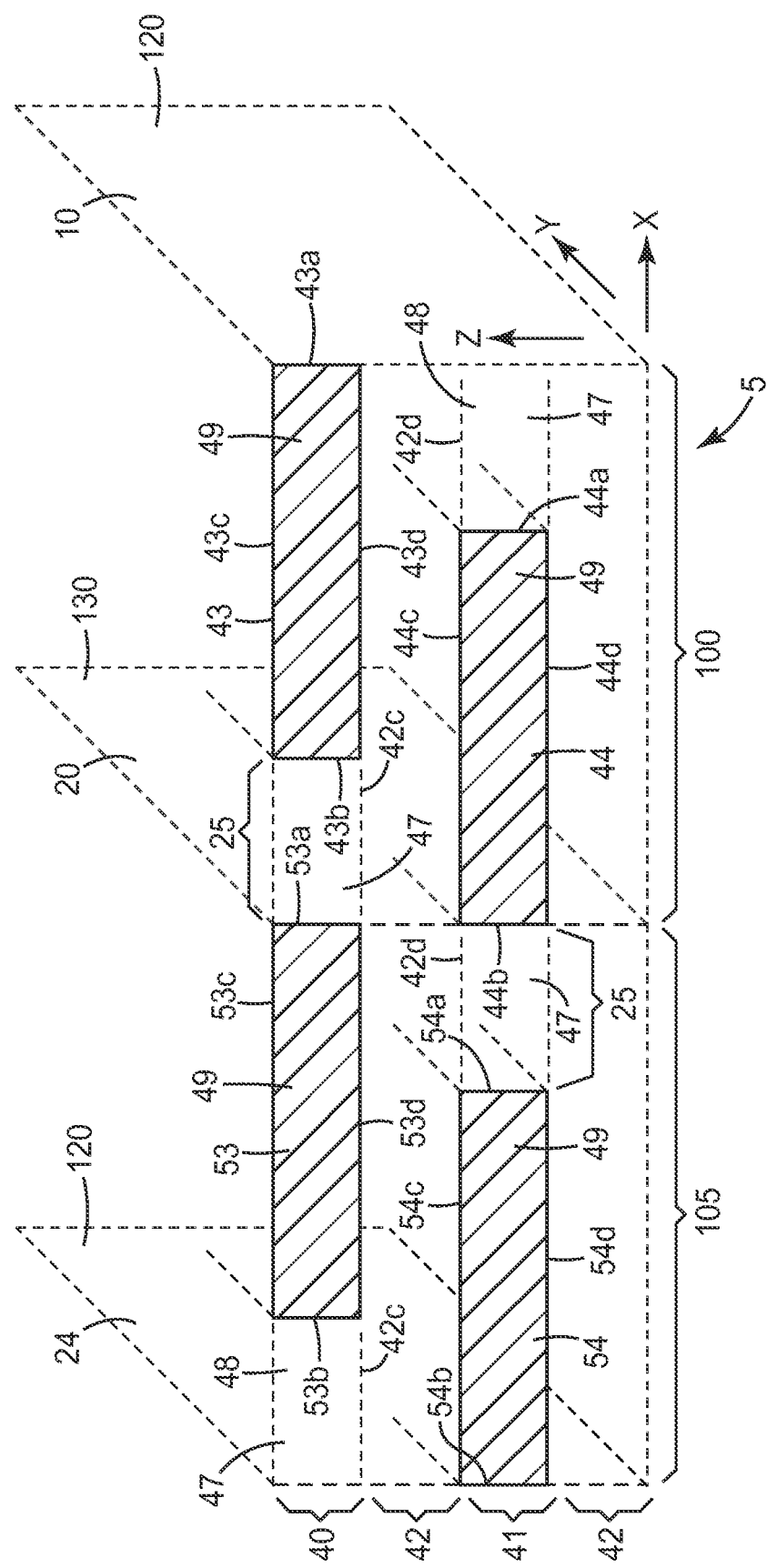
FIG. 5 is a schematic representation of an electroactive actuator having at least two electrically responsive elements.

A representative electroresponsive actuator 5 comprises first 100 and second 105 electrically responsive elements as illustrated in FIG. 5. An electrically responsive element 100 is further described in U.S. Pat. No. 4,627,138 (Im); U.S. Pat. No. 5,997,880 (Friedl et al.); U.S. Pat. No. 5,153,859 (Chatigny et al.); and International Publication No. WO 02/096647A1 (Hilmas et al.). Electroresponsive actuator 5 comprises first 100 and second 105 electrically responsive elements, which are unpoled, and extend along an x-dimension. Each of the electrically responsive elements 100, 105 has three mutually orthogonal dimensions, an x-, a y- and a z-dimension. The elements 100, 105 contain alternating conductive 40, 41 and nonconductive 42 layers. The conductive layers 40, 41 comprise regions 43, 53, 44, 54 of polymeric conductive material 49 and regions 48 of polymeric nonconductive material 47; and the nonconductive layer 42 comprises polymeric nonconductive material 47. The electroresponsive actuator 5 further comprises a cutting plane 20 which is useful for separating the first 100 and second 105 elements. The cutting plane 20 is perpendicular to the x-dimension and parallel to the y-z plane.

The first 40 and second 41 conductive layers each have conductive regions 43, 53, 44, 54. The first conductive layer 40 has first 43 and second 53 conductive regions, and the second conductive layer 41 has third 44 and fourth 54 conductive regions. The conductive regions 43, 53, 44, 54 are arranged as illustrated in FIG. 5, so that a first surface 43a, 53a of first 43 and second 53 conductive regions of first conductive layer 40 and a second surface 44b, 54b of third 44 and fourth 54 conductive regions of second conductive layer 41 are alternatingly exposed to one of two opposing faces 120, 130 of the elements 100, 105. The first 120 and second 130 faces are coincident to first 43a, 53a and second surfaces 44b, 54b of each respective conductive region 43, 53 and 44, 54. Further, first 120 and second 130 opposing faces are parallel to the cutting 20, 24 and reference planes 10. The two faces 120, 130 are exposed to recover a single electronically responsive element 100 after separation at one or more cutting planes 20 or at a reference plane 10 and a cutting plane 20.

The x-dimension refers to the width or cross-web dimension, the y-dimension refers to the depth or down-web dimension, and the z-dimension refers to the thickness or height of the electroresponsive actuator 5 having at least two electrically responsive elements 100, 105. Analogously, the y-z plane corresponds to a plane having y- and z-dimensions, whereas an x-z plane corresponds to a plane having x- and z-dimensions. The x-y plane corresponds to a plane having x- and y-dimensions.

The x-dimension of the electroresponsive actuator 5 comprising at least two elements 100, 105 refers to the width or cross-web dimension of the electroresponsive actuator 5, and the subsequent electrically responsive elements 100, 105 resulting from the electroresponsive actuator 5 after separating at a cutting plane 20. The x-dimension of an element 100 may be in a range of 0.01 micrometer to 1 centimeter. Preferably, the x-dimension is in a range of 1 micrometer to 0.1 centimeter, and more preferably, the x-dimension is in a range of 10 micrometers to 0.01 centimeter.

The y-dimension relates to the length or down-web dimension of an article comprising at least two elements 100, 105. The y-dimension also refers to the elements 100, 105 after separation by a cutting plane 20 from the electroresponsive actuator 5. The elements 100, 105 may each have a specific y-dimension as determined by a given application. The element 100 may be separated from the electroresponsive actuator 5 in the x-z plane, which is perpendicular to the y-dimension. The y-dimension of the element 100 may be in a range of 0.01 micrometer to 1 centimeter. Preferably, the y-dimension is in a range of 1 micrometer to 0.1 centimeter, and more preferably, the y-dimension is in a range of 10 micrometers to 0.01 centimeter.

The z-dimension relates to the thickness or height of an electroresponsive actuator 5 comprising at least two electronically responsive elements 100, 105. The z-dimension may vary with respect to the number of alternating layers of conductive and nonconductive material as the material is extruded through a die orifice of an extrusion apparatus and the degree of drawdown of the multiple layers during coextrusion. The z-dimension of each of the elements 100, 105 may be in a range of 3 micrometers to 3 millimeters. The z-dimension of the electroresponsive actuator 5 after exiting the die orifice may be different relative to the z-dimension of the electroresponsive actuator 5 after draw down. Preferably, the z-dimension is in a range of 10 micrometer to 0.5 millimeters, and more preferably, the z-dimension is in a range of 25 micrometer to 0.05 millimeters.

In FIG. 5, the first 100 and second 105 electrically responsive elements of electroresponsive actuator 5 have first 20 and second 24 cutting planes, and a reference plane 10. The reference plane 10 of the article may also function as one of the cutting planes 20, 24. The reference 10 and cutting planes 20, 24 each are parallel with respect to one other in the y-z plane, and similarly to the faces 120, 130 of the elements 100, 105. The reference 10 and cutting 20, 24 planes separate the elements 100, 105 from one other exposing the alternating layers of conductive material 49 of the conductive layers 40, 41 on one of the two faces 120, 130. Separation of the elements 100, 105 may be accomplished with techniques including die cutting, laser cutting, shear slitting, score slitting, hot wire engaged slitting and combinations thereof. A trim portion or inoperative element of the electroresponsive actuator 5 extending in the x-direction away from either of the faces 120, 130 may result after separation of the elements 100, 105 at a reference 10 or cutting 20, 24 planes. The trim portion or inoperable element may comprise irregularly shaped surfaces or faces formed during extrusion through a die orifice and drawdown of the electroresponsive actuator 5. The trim portion may be recycled for other applications.

The electroresponsive actuator 5 contains alternating conductive 40, 41 and nonconductive 42 layers extending in the z-dimension as illustrated in FIG. 5. The alternating conductive 40, 41 nonconductive 42 layers are continuous in the y-dimension. The conductive layers 40, 41 are discontinuous in the x-dimension, and comprise polymeric conductive material 49. The nonconductive layer 42 comprises nonconductive polymeric material 47 which is continuous in the x-dimension.

The first 40 and second 41 conductive layers of FIG. 5 each comprise at least two conductive regions. The first conductive layer 41 contains first 43 and second 53 conductive regions, and the second conductive layer 41 contains third 44 and fourth 54 conductive regions. Conductive regions 43, 53 and 44, 54 are discontinuous in the x-dimension, and continuous in the y-dimension. First conductive region 43 of the first conductive layer 40 has a first surface 43a, second surface 43b, a third surface 43c, and a fourth surface 43d. Second conductive region 53 of the first conductive layer 40 has a first surface 53a, second surface 53b, a third surface 53c, and a fourth surface 53d. Conductive regions 43, 53 are discontinuous in the x-dimension having interstices 25 containing nonconductive material 47. Similarly, third conductive region 44 of the second conductive layer 41 has a first surface 44a, second surface 44b, a third surface 44c and a fourth surface 44d. Fourth conductive region 54 of the second conductive layer 41 has a first surface 54a, a second surface 54b, a third surface 54c, and a fourth surface 54d. Third and fourth conductive regions 44, 54 are also discontinuous in the x-dimension having interstices 25 containing nonconductive material 47. Nonconductive layer 42 comprises nonconductive material 47 which extends continuously in the x- and y-dimensions.

A cross-section of electroresponsive actuator 5 as illustrated in FIG. 5 has at least two electrically responsive elements 100, 105 in the x-z plane. The cross-section shows a nonconductive layer 42 having a third 42c and fourth 42d surfaces. The nonconductive layer 42 is located in between a first 40 and second 41 conductive layers. The first conductive layer 40 is adjacent to the third surface 42c of the nonconductive layer 42, and the second conductive layer 41 is adjacent to the fourth surface 42d of the nonconductive layer 42. The first conductive layer 40 has at least first 43 and second 53 conductive regions, and the second conductive layer 41 has at least third 44 and fourth 54 conductive regions, where the interstices 25 between conductive regions 43, 53, 44, 54 may contain a polymeric nonconductive material 47. Conductive regions 43, 53 and 44, 54 of conductive layers 40 and 41, respectively, repeat in the x-dimension.

Figure 6:
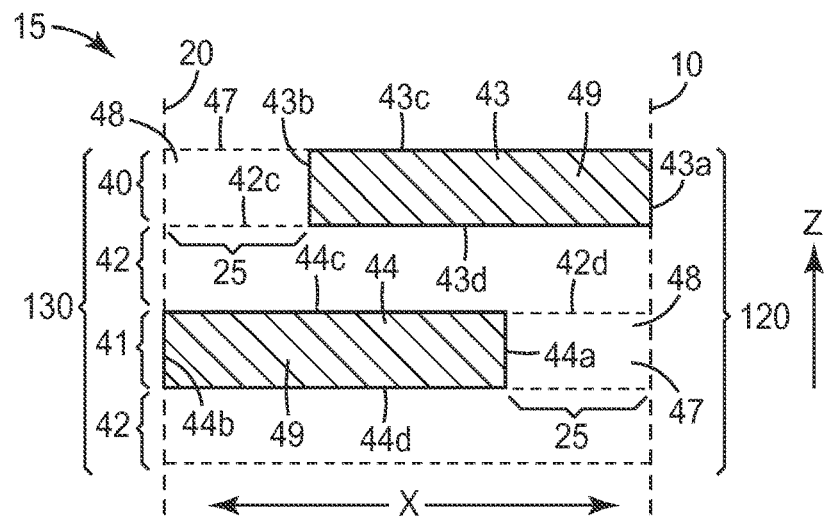
FIG. 6 is a schematic representation of a unit cell.

FIG. 6 illustrates an electrically responsive element 100, 105 of an electroresponsive actuator 5, where each element 100, 105 is made from a unit cell 15. The unit cell 15 comprises at least one nonconductive layer 42 comprising nonconductive material 47, which has third 42c and fourth 42d surfaces that are continuous along two substantially orthogonal axes, the x- and y-dimensions. The unit cell 15 further comprises at least first 40 and second 41 conductive layers comprising conductive material 49 that are discontinuous in the x-dimension, where the first conductive layer 40 comprises a first conductive region 43, and the second conductive layer 41 comprises a third conductive region 44. First conductive region 43 has a first surface 43a, a second surface 43b, a third surface 43c, and a fourth surface 43d. Third conductive region 44 has a first surface 44a, a second surface 44b, a third surface 44c, and a fourth surface 44d. The first surface 43a of the first conductive region 43 of the first conductive layer 40 is coincident with a reference plane 10, where the second surface 43b of the first conductive region 43 does not extend to the cutting plane 20. The second surface 44b of the third conductive region 44 of the second conductive layer 41 is coincident with a cutting plane 20, where the first surface 44a of the third conductive region 44 does not extend to the reference plane 10. The reference 10 and cutting 20 planes are parallel in a y-z plane. The unit cell 15 comprises alternating layers having a nonconductive layer 42 in between the first conductive layer 40 and the second conductive layer 41.

The unit cell 15 of FIG. 6 comprises first 120 and second 130 opposing faces. The first face 120 is parallel to the reference plane 10, and the second face 130 is parallel to a cutting plane 20. The reference 10 and cutting 20 planes are parallel in the y-z plane. Electrically responsive elements 100, 105 are separable at a cutting plane 20 and/or reference plane 10 where the first surface 43a of the first conductive region 43 and the second surface 44b of the third conductive region 44 are exposed on the first 120 and second 130 opposing faces, respectively.

The unit cell 15 of FIG. 6 illustrates a nonconductive layer 42 having a third surface 42c adjacent to the fourth surface 43d of the first conductive region 43 of the first conductive layer 40. The fourth surface 42d of the nonconductive layer 42 is adjacent to the third surface 44c of the third conductive region 44 of the second conductive layer 41. The interstices 25 may contain polymeric nonconductive material 47.

The electronically responsive elements 100, 105 of the electroresponsive actuator 5 of FIG. 5 are unpolarized for use as components of a group selected from actuators, sensors, pyroelectric devices, capacitors, and piezoelectric devices. These elements 100, 105 typically comprise alternating layers of conductive and nonconductive materials. The number of layers of an element 100 may be defined by the design of the layering assembly used with appropriate extrusion equipment or other process considerations. Similarly, the dimensions of an element 100 may be subject to the design of a particular construction and a defined user application.

In one embodiment, the conductive 40, 41 and nonconductive 42 layers of an element 100 of FIG. 5 have controlled thicknesses. The thickness of the layers is based on the layering assembly 400 design and corresponding downstream extrusion equipment. The element 100 preferably has conductive layers 40, 41 that are as thin as possible for subsequent use in a device without losing conductivity. The nonconductive 42 and conductive 40, 41 layers are typically symmetrical and preferably as thin as possible in order to maximize the electrical conductivity of the elements within a device. The first 120 and second 130 opposing faces are used to separate first 100 and second 105 elements at cutting planes 20, 24 and/or reference plane 10. The cutting 20, 24 and/or reference 10 planes expose the first surface 43a of first conductive region 43, and the second surface 44b of the third conductive region 44 to the first 120 and second 130 opposing faces of the elements 100, 105 as illustrated in FIG. 6.

Figure 7:
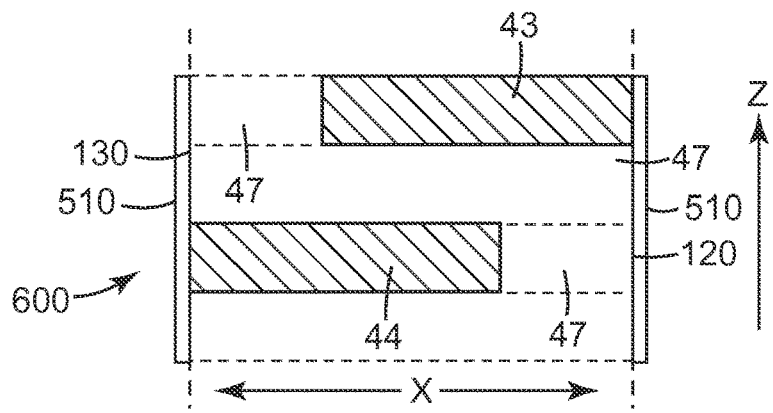
FIG. 7 is a schematic representation of a first device having a conductive coating on both faces.

In one embodiment, the unit cell 15 of FIG. 6 may be used as component of a first device 600 illustrated in FIG. 7. The first device 600 may be coated with a second conductive material 510 on the first 120 and second 130 opposing faces. The first surface 43a of the first conductive region 43 and the second surface 44b of the third conductive region are exposed at the first 120 and second 130 faces of FIG. 6, respectively. The first device 600 may comprises additional alternating conductive 40, 41 and nonconductive 42 layers extending in the z-direction.

The second conductive material 510 used to electrically interconnect the exposed surfaces 43a, 44b of the conductive regions 43, 44 of FIG. 7 on faces 120, 130 may be of many types. Examples include, but are not limited to, solder, silver, other conductive metals, conductive polymers and polymers containing conductive fillers. The second conductive material 510 is preferably applied across each of the opposing faces 120, 130 so as to electrically interconnect all of the exposed surfaces 43a, 44b of the conductive regions 43, 44 to either of the faces 120, 130. Conducting wires may be further attached to the second conductive material 510 followed by poling of the first device 600.

Figure 8:
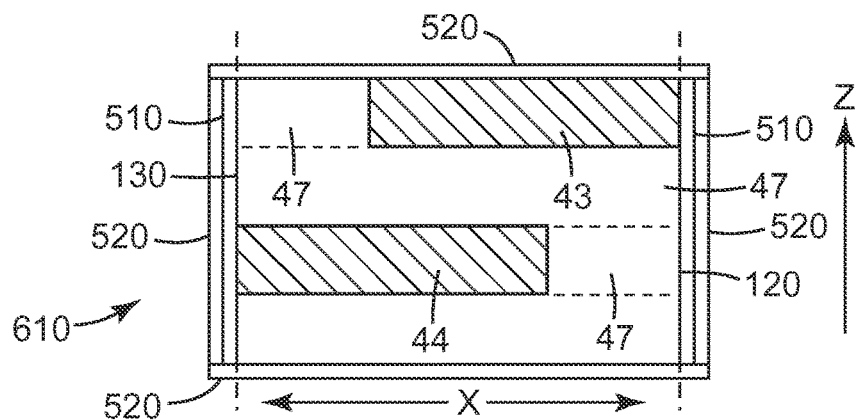
FIG. 8 is a schematic representation of a second device coated with an insulative layer.

FIG. 8 illustrates a second device 610 having an insulative coating or layer 520. The device 610 may be further coated with an insulative layer 520 on faces 120, 130 and any remaining faces in the x-y and x-z planes. The insulative layer 520 of second device 610 assists in reducing moisture and vapor penetration of the first and second conductive layers 40, 41, as well as to reduce the possibility of electrical discontinuity across the second device 610.

A device 610 comprising an element 100 having thin layer thicknesses typically has a voltage level of less than 10 volts. As the thickness of the layers decreases, the lower the applied driving voltage needed for a given application. The device 610 may also have a modulus of elasticity in a range of 0.1 MPa-10 GPa.

Figure 9:
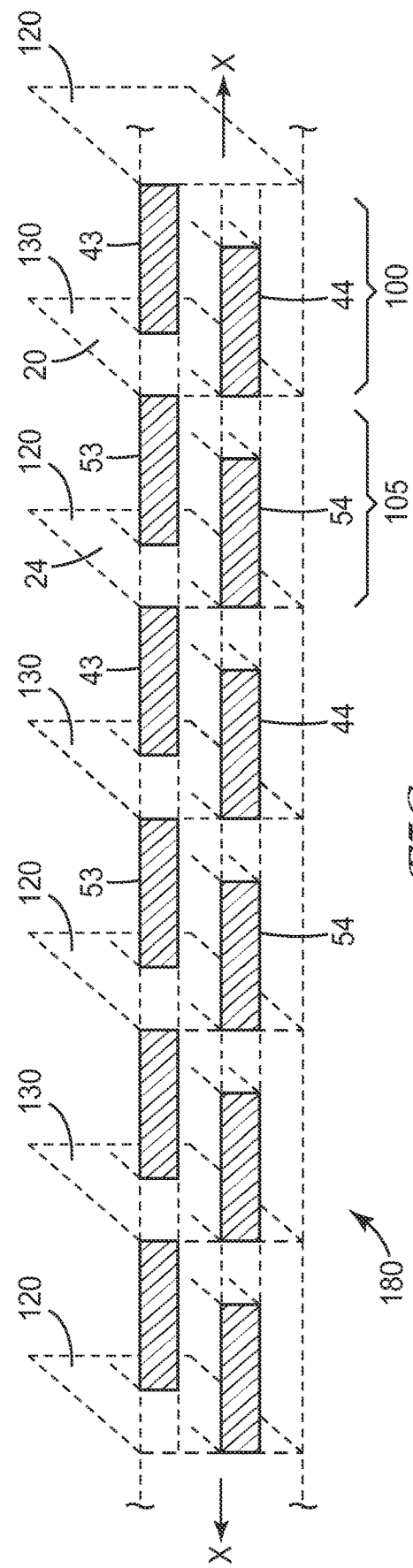
FIG. 9 is a schematic representation of an article comprising electrically responsive elements repeating in the x-dimension.

FIG. 9 illustrates an article 180 having at least first 100 and second 105 electrically responsive elements, where the elements 100, 105 are repeating in the x-dimension. The elements 100, 105 are separable by one or more cutting planes 20, 24. The exposed first 120 and second 130 opposing faces of the elements 100, 105 result from separation of the elements 100, 105 at the cutting 20, 24 and/or reference 10 planes. First conductive layer 40 comprises first 43 and second 53 conductive regions which are discontinuous in the x-dimension. Similarly, third 44 and fourth 54 conductive regions of the second conductive layer 41 are discontinuous in the x-dimension. The elements 100, 105 are made from the unit cell 15 as illustrated in FIG. 6.

In one embodiment, the electroresponsive actuator 5 of FIG. 5 contains a plurality of electronically responsive elements 100, 105, where the elements are separable by n−1 cutting planes 20, 24. The cutting planes 20, 24 are perpendicular to the x-dimension of the article. A plurality of elements 100, 105 comprises n unit cells 15 having n−1 cutting planes 20, 24, wherein n is at least 3.

Figure 10:
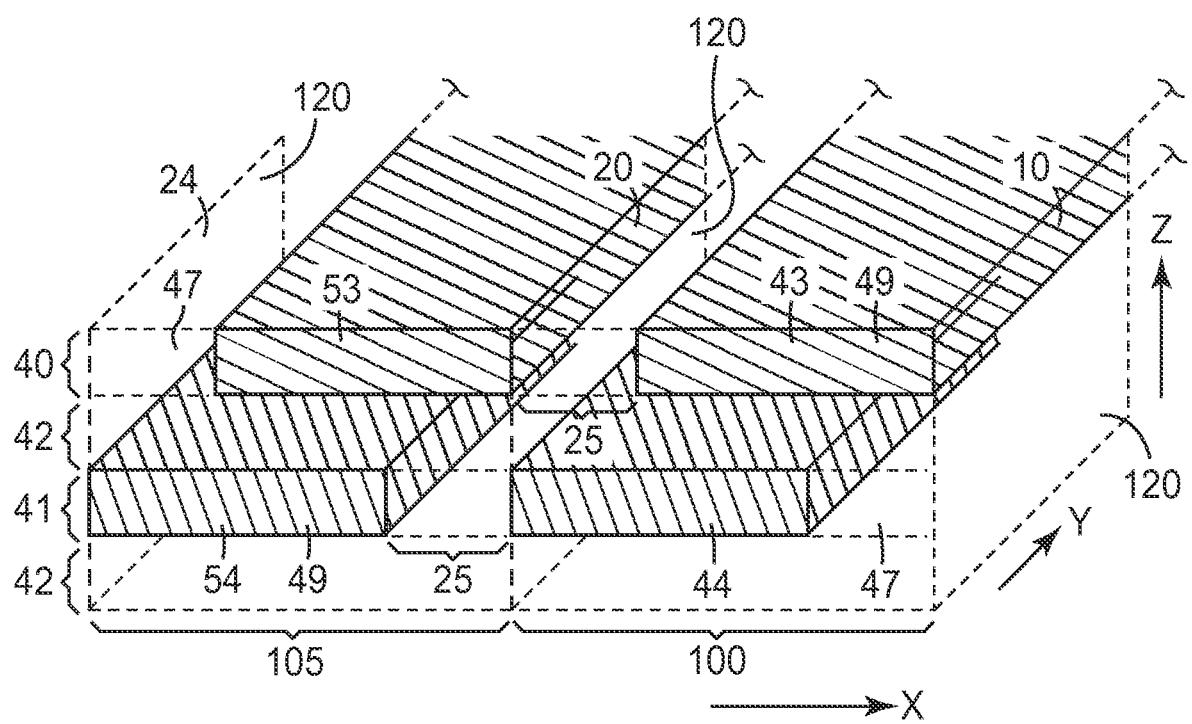
FIG. 10 is a schematic representation of an article having at least two electrically responsive elements presented in the x-, y- and z-dimensions.

In one embodiment, article 180 comprises first 100 and second 105 electrically responsive elements repeating in the x-dimension of FIG. 9. The elements preferably comprise symmetrical nonconductive 42 and conductive 40, 41 layers. Preferably, the electrically responsive elements 100, 105 repeat in the x-dimension in a range of 2 to 1000 unit cells 15. More preferably, the elements 100, 105 repeat in a range of 5 to 500 unit cells 15, and more preferably in a range of 25 to 250 unit cells 15. Further, the elements 100, 105 extend continuously in the y-dimension as illustrated in FIG. 10. The unit cells 15 may extend in the z-dimension resulting from the number of nonconductive 42 and conductive 40, 41 layers selected as well as the thickness of the individual layers after symmetrically drawing down the nonconductive 42 and conductive 40, 41 layers through an extrusion die.

FIG. 10 illustrates a three-dimensional perspective of electroresponsive actuator 5 having at least two electrically responsive elements 100, 105 separable at cutting 20, 24 and reference 10 planes. Conductive layers 40, 41 are continuous in the y-dimension, and discontinuous in the x-dimension. Nonconductive layer 42 alternates with the conductive layers 40, 41 where the nonconductive layer 42 is continuous in the x- and y-dimensions. Nonconductive material 47 occupies the interstices 25 between conductive regions 43, 53 of first conductive layer 40, and conductive regions 44, 54 of the second conductive layer 41.

Figure 11:
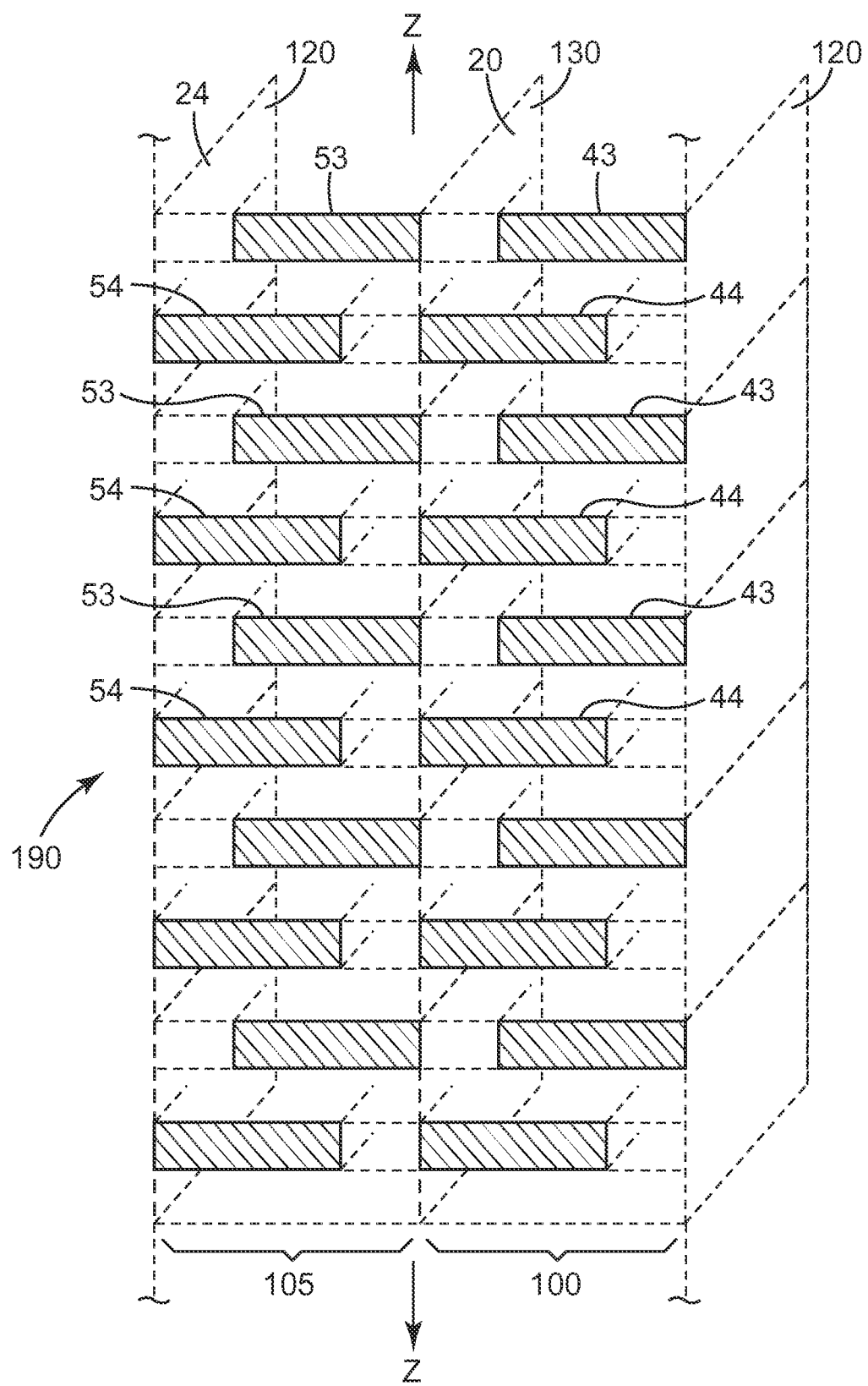
FIG. 11 is a schematic representation of an article comprising electrically responsive elements repeating in the z-dimension.

FIG. 11 illustrates article 190 having at least first 100 and second 105 electrically responsive elements, where the elements 100, 105 have alternating conductive 40, 41 and nonconductive 42 layers repeating in the z-dimension. The elements 100, 105 are separable at cutting planes 20, 24. As similarly illustrated in FIG. 5, the first 40 conductive layer comprises first 43 and second 53 conductive regions, and the second 41 conductive layer comprises third 44 and fourth 54 conductive regions repeating in the x-dimension. The cutting planes 20, 24 for separating the elements 100, 105 are perpendicular in the x-dimension. The separation of the elements 100, 105 along cutting planes 20, 24 of article 190 may result in multilayered elements for specific applications.

Figure 12:
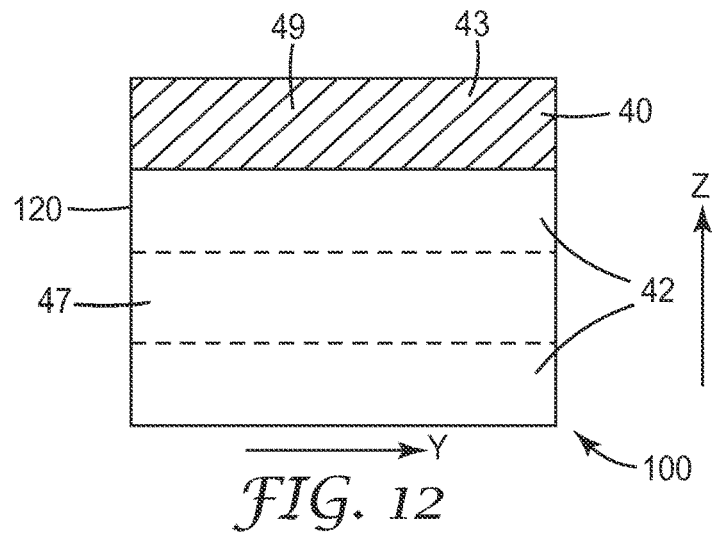
FIG. 12 is a schematic representation of an unit cell viewed in the y-z plane along face 120.

FIG. 12 illustrates a cross-sectional view in the y-z plane of element 100. The first face 120 of element 100 shows alternating conductive 40 and nonconductive 42 layers. In the y-z plane, the layers include a first conductive layer 40, and a nonconductive layer 42. In the z-dimension, the element 100 comprises first conductive layer 40, nonconductive layer 42, nonconductive material 47 of nonconductive region 48 of second conductive layer 41 as illustrated in FIG. 5, followed by a nonconductive layer 42. Nonconductive material 47 may fill the interstices 25 or nonconductive region 48 located between the conductive regions of the first conductive layer 40, where a conductive region does not extend to the reference plane 10 of first face 120. Conductive layer 40 comprises polymeric conductive material 49 of first conductive region 43, which is continuous in the y-dimension. Multiple alternating conductive 40 and nonconductive 42 layers may be coextruded for forming a multilayered element 190 extending in the z-dimension of FIG. 11.

Figure 13:
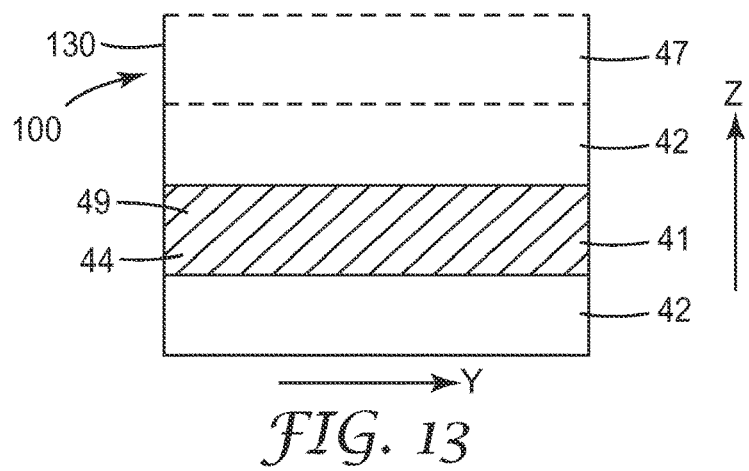
FIG. 13 is a schematic representation of an unit cell viewed in the y-z plane along face 130.

FIG. 13 illustrates a cross-sectional view in the y-z plane of element 100. The second face 130 of element 100 shows alternating conductive 41 and nonconductive 42 layers. In the y-z plane, the layers include nonconductive material 47 of nonconductive region 48 of first conductive layer 40 as illustrated in FIG. 5, a nonconductive layer 42, and a second conductive layer 41, followed by a nonconductive layer 42. Nonconductive material 47 fills the interstices 25 or nonconductive region 48 of first conductive layer 40 of FIG. 12 between the conductive regions. Second conductive layer 41 comprises polymeric conductive material 49 of third conductive region 44, which is continuous in the y-dimension.

Figure 14:
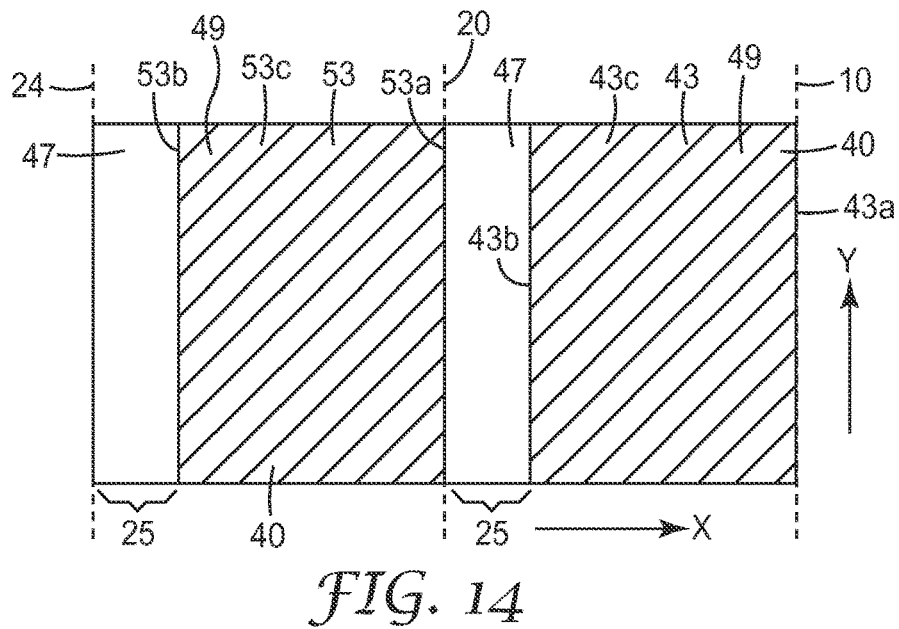
FIG. 14 is a schematic representation of a top view of an article having two electrically responsive elements as viewed in an x-y plane.

FIG. 14 illustrates a cross-sectional view in an x-y plane of electroresponsive actuator 5 comprising at least first 100 and second 105 electrically responsive elements separable at cutting planes 20, 24 and/or reference plane 10. Elements 100, 105 are shown with first 43 and second 53 conductive regions of the first conductive layer 40 having interstices 25 filled with a nonconductive material 47. The first surface 43a of the first conductive region 43 is coincident with reference plane 10, where the second surface 43b does not extend to the first cutting plane 20. Similarly, the first surface 53a of second conductive region 53 of the first conductive layer 40 is coincident with the first cutting plane 20, where the second surface 53b does not extend to the second cutting plane 24. Third surface 43c of a first conductive region 43 and third surface 53c of second conductive region 53 are the uppermost surfaces in the x-y plane illustrated in FIG. 14.

Each of the alternating conductive layers 40, 41 may be made of different materials or combinations of materials which may further comprise particles or fillers for conductivity. Similarly, each of the nonconductive layers 42 may include the analogous material or combination of materials to that used in the conductive layers 40, 41, although each individual nonconductive layer 42 may include different materials or combinations of materials from the other nonconductive layers. The nonconductive layers 42 may further comprise particles to enhance electrical conductivity of an element 100 of a device.

In one embodiment, the first polymeric material and organic particles form a polymeric conductive material 49 of the conductive layers 40, 41.

In one embodiment, a first polymeric material is elastomeric.

Thermoplastic materials that have elastomeric properties are typically called thermoplastic elastomeric materials. Thermoplastic elastomeric materials are generally defined as materials that exhibit high resilience and low creep as though they were covalently crosslinked at ambient temperatures, yet process like thermoplastic nonelastomers and flow when heated above their softening point. Thermoplastic elastomeric materials useful in the conductive layer and/or the nonconductive layer as a first polymeric material or one of a blend of polymeric materials include, for example, linear, radial, star, and tapered block copolymers such as those described below.

Examples of a first polymeric material include silicone elastomers, acrylic elastomers, polyurethanes, polybutadienes, thermoplastic elastomers, polybutadiene-acrylonitrile copolymers and combinations thereof.

In one embodiment a first polymeric material is a thermoplastic.

Examples of a thermoplastic first polymeric material include pressure sensitive adhesives, fluoropolymers and polymers comprising silicone and acrylic moieties, and the like. Examples of fluoropolymers include homopolymers such as polyvinylidene difluoride (PVDF), copolymers such as polyvinylidene fluoride-trifluoroethylene P(VDF-TrFE), polyvinylidene fluoride-chlorofluoroethylene P(VDF-CFE), polyvinylidene fluoride-hexafluoropropylene P(VDF-HFP), polyvinylidene fluoride-trifluoroethylene-chlorofluoroethylene P(VDF-TrFE-CFE), polyvinylidene fluoride-trifluoroethylene-chlorotrifluoroethylene P(VDF-TrFE-CTFE), polyvinylidene fluoride-tetrafluoroethylene-chlorotrifluoroethylene, polyvinylidene fluoride-trifluoroethylene-hexafluoropropylene, polyvinylidene fluoride-tetrafluoroethylene-hexafluoropropylene, polyvinylidene fluoride-trifluoroethylene-tetrafluoroethylene, polyvinylidene fluoride-tetrafluoroethylene, polyvinylidene fluoride-trifluoroethylene-vinyl fluoride, polyvinylidene fluoride-tetrafluoroethylene-vinyl fluoride, polyvinylidene fluoride-trifluoroethylene-perfluoro(methyl vinyl ether), polyvinylidene fluoride-tetrafluoroethylene-perfluoro(methyl vinyl ether), polyvinylidene fluoride-trifluoroethylene-bromotrifluoroethylene, polyvinylidene fluoride-tetrafluoroethylene-bromotrifluoroethylene, polyvinylidene fluoride-tetrafluoroethylene-chlorofluoroethylene, polyvinylidene fluoride-trifluoroethylene-vinylidene chloride, and polyvinylidene fluoride-tetrafluoroethylene-vinylidene chloride and combinations thereof.

Examples of organic conductive particles or fillers include graphite, carbon nanotubes, carbon black, and combinations thereof. These materials may be added to the first polymeric material to form a polymeric conductive material 49 for the conductive layers 40, 41. The first polymeric material may be mixed, blended, compounded or by other means with organic materials or fillers to achieve a uniform mixture of materials suitable for forming conductive layers 40, 41.

In one embodiment, the first polymeric material may be blended or mixed with inorganic particles to form conductive layers 40, 41. Examples of inorganic particles or fillers include silver, copper, nickel, aluminum, platinum, palladium, derivatives and combinations thereof. These materials may have irregular shapes or defined structures suitable for forming conductive layers 40, 41.

In one embodiment, the first polymeric material may be blended or mixed with inorganic coated particles to form conductive layers 40, 41. Examples of inorganic materials used for coating particles include gold, silver, palladium, platinum and combinations thereof.

In one embodiment, the first polymeric material may form the polymeric conductive material 49 of the conductive layers 40, 41. Examples of a first polymeric material, which is conductive include poly(3,4-ethylenedioxy thiophene), polyaniline, polypyrrole, polythiophene, polydiacetylene, polyacetylene, polyisothianaphthene, polyheteroarylene-vinylene, wherein the heteroarylene group can for example be thiophene, furan or pyrrole, poly-p-phenylene, polyphenylene sulphide, polyperinaphthalene, polyphthaloxyanine, copolymers of and physical mixtures thereof. The first polymeric material may be conductive with optional particles or fillers.

Optional additives to combine with the conductive first polymeric material may further include dopants, doping agents and combinations thereof. Doping agents comprises iodine, peroxides, Lewis acids and protic acids for doping by oxidation, sodium, potassium and calcium for doping by reduction.

The nonconductive layer 42 comprises a polymeric nonconductive material 47. The polymeric nonconductive material 47 may comprise a first polymeric material as described above. Mixtures or blends of the first polymeric material with other polymeric materials may be utilized to form a nonconductive layer 42. Additives to increase the dielectric constant may be added or compounded with the first polymeric material of nonconductive layer 42. Examples additives include $BaTiO_3$, lead zirconate titanate (PZT), PT (lead titanate) composites, PTCa and combinations thereof. These additives may be compounded with the first polymeric material.

The conductive polymeric material 49 and the nonconductive polymeric material 47 have sufficient viscosity to be extruded or coated onto an adjacent layer of the electroresponsive actuator 5. An extrudable formulation of a blend of conductive polymeric materials 49, as well as a blend of a conductive polymeric material 49 with a nonconductive material 47 may be utilized.

The first polymeric material of the conductive layers 40, 41 may include conductive polymers, polymeric materials or a blend of polymeric materials rendered conductive. In some instances, the first polymeric material is mixed with organic materials to yield a conductive layer.

The nonconductive 42 and conductive 40, 41 layers being continuous in the y-dimension or the down-web dimension are substantially uniform in thickness to plus or minus 10 percent. Similarly, it is desirable to have thin conductive layers, where the thickness of these layers may be governed by the average diameter or size of the particles to be blended with the first polymeric materials.

The multilayer construction can be obtained by multilayer extrusion process as described in U.S. Pat. No. 4,627,138. In another multilayer extrusion process, the conductive layer (also referred to as an electrode) can be patterned as further described in U.S. Pat. No. 7,777,397 and incorporated by reference in its entirety. This process helps to control of the desired size of actuator rather than having full width depending upon the die lip as described in above patent. Methods for coextruding multiple layer webs, and related equipment are described in U.S. Pat. No. 6,949,283 (Kollaja et al.) U.S. Pat. No. 5,825,543 (Ouderkirk et al.) and U.S. Pat. No. 5,783,120 (Ouderkirk et al.).

Multilayer construction can also be achieved by laminating each electroactive layer having electrode layers on the top and bottom. The lamination process can be done in multiple ways such as using adhesive, heat lamination, using solvent (such as described in U.S. Pat. No. 5,997,800) to soften the top surface.

Micropumps

The micropumps used in connection with the medical dressings of the present invention may take any suitable form. In some embodiments, the micropumps may be portable, self-contained devices, while in other embodiments the micropumps may be fixed, stationary systems. In some instances, fluids may even be removed from a sealed environment defined by the medical dressings using suction developed by a person using their mouth (in, e.g., a battlefield or other remote location).

Examples of some potentially suitable micropumps that may be used with and/or supplied in a kit with the medical dressings of the present invention may include the pumps described in U.S. Patent Application Publication No. US 2007/0209326 (Tretina), although many other pumps may be used in place of the pumps disclosed therein. Although the pumps described in the document identified above include a power source (e.g., a battery), micropumps used in connection with the present invention may be manually powered. Examples of some other potentially suitable manually powered pumps may include, e.g., devices that include resilient cavities that can be compressed and, when returning to their pre-compression states, provide a vacuum force at the inlet of the pump (e.g., bulbs, hemovacs, etc.).

In some embodiments, the wound dressing and micropump system of the present invention may preferably include one or more traps or fluid collection components capable of collecting and retaining liquids (and, in some embodiments, gases) removed from the sealed environments defined by the medical dressings. The traps may be integral with the micropumps in some embodiments, while in other embodiments the traps may be separate from the micropumps such that the traps may be replaced without requiring replacement of both the micropumps and the traps. Examples of some potentially suitable traps that are designed to separate liquids from the removed fluids may be described in, e.g., U.S. Patent Application Publication Nos. US 2007/0209326 (Tretina) and US 2007/0172157 (Buchman).

It may be preferred that the medical dressings of the present invention and any micropumps used therewith to remove fluids from sealed environments be capable of quickly connecting with each other to form a fluid-tight seal during removal of fluids from the sealed environments defined by the medical dressings. The medical dressing itself may preferably be featureless (e.g., present only the smooth external surface of the backing), while the micropump includes a seat that provides a surface capable of sealing against the featureless backing to form the required fluid-tight seal.

In some embodiments, the medical dressings and micropumps may include more conventional connections/fittings to provide a fluid-tight connection between the micropumps and the medical dressings. Such fittings may be useful where, e.g., the micropump is to be connected to the medical dressing for an extended period of time, e.g., for more than 2 minutes. In such an embodiment, the wound dressing may include a fitting that attaches to the external surface of the backing using, e.g., a pressure sensitive adhesive, etc. The fitting may, for example, include a tubing connector, Luer lock fitting, etc. designed for longer-term connection to a micropump. The adhesive used to attach the fitting to the medical dressing may be releasable, i.e., the fitting may potentially be removed from the dressing while the dressing remains in place over a wound, such that any sealed environment defined by the medical dressing remains intact during removal of the fitting.

Preferred pumps are micropumps. Preferred micropumps are diaphragm pumps having at least one deformable element. These micropumps may be actuated by a number of means including the use of electroactive polymers (EAP), piezoelectric pumps using ceramic piezoelectric elements such as PZT, ionic Polymer Metal Composites (IMPC) as well as composites incorporating carbon nanotubes or other conductive elements that enhance the electroactive response.

Other preferred pumps include the Digital Pulse Activated Cell system pumps disclosed in US 2004/0234401, WO2006/065884, and US 2005/045210, the EAP Micropumps disclosed in herein which preferably comprise multilayer EAP elements made, for example, as taught in U.S. Pat. No. 4,627,138 as well as EAP pumps disclosed in Pope et. al. Dielectric Elastomer Laminates for Active Membrane Pump Applications, Proc. Of SPIE Vol. 5385, 2004, pp 60-67; traveling wave pumps such as that described in U.S. Pat. No. 5,961,298. Suitable EAP materials include polyurethanes such as those disclosed in U.S. Pat. No. 5,977,685, polyacrylates such as 3M Company VHB adhesive #4905, polyvinylidene fluoride (PVDF), polyvinylidene/trifluoroethyelne (VDF-TrFE), and silicones such as Nusil CF19-2186.

The micropump comprises an inlet, an exit, and optionally a means for regulating the pressure. The micropump may be attached directly to the dressing or may be remote from the dressing but in fluid communication with the dressing by suitable means such as a tube. The micropump preferably comprises a one way inlet valve and a one way exit valve to ensure fluid is evacuated and not allowed to flow back into the wound bed. The valves may be of any design such conventional ball valves. Preferably, the valves are comprised of elastomeric elements (as described herein). For example, preferred valves are umbrella or duckbill valves such as those available from Vernay Laboratories of Yellow Springs, Ohio.

A check valve or other means may be required to regulate pressure, particularly for pumps able to create a vacuum of more than 100 mmHg below atmospheric pressure. This may be accomplished via a check valve that opens at a predetermined pressure drop and allows air into the wound bed. If a check valve is used it preferably has a membrane element that will filter out microorganisms and prevent them from entering the wound bed. Alternatively and preferably the micropump is equipped with a pressure sensor and a control circuit that slows the pump speed at a predetermine pressure set point. The set point is preferably variable and easily set by the clinician. A read out of the pressure may be desired. Alternatively, the micropump is self limiting and unable to create a vacuum more than the desired maximum vacuum, e.g. more than about 150 mmHg.

The micropump may be driven by AC or DC power and may be from a line or battery source. Preferably the micropump is driven by a small disposable battery source. The power source may be located in a package with the micropump or it may be at a remote site and connected to the micropump. Preferably, the battery is capable of driving the micropump for at least 2 hours of continuous operation. More preferably, the battery is capable of driving the micropump for at least 8 hours, even more preferably at least 1 day, more preferably still for multiple days of continuous operation. Thus, the micropumps are more energy efficient to avoid the need for large battery sources.

The micropump is preferably programmable to pull a continuous, intermittent or variable vacuum. For example, the micropump could be programmed to pull and hold a vacuum of 100 mmHG or be programmed to pull a vacuum of 150 mmHg for a period of time following by a period of time at a vacuum of 25 mmHg below atmospheric pressure in an oscillatory fashion.

In a preferred embodiment, the micropump is secured directly to the wound dressing either through the interior portion of the dressing or at the periphery. In either case an inlet tube may be unnecessary. The micropump also can be remote from the dressing and attached via an inlet tube. In such case, the micropump may have multiple inlets and exit ports and/or multiple micropumps may be employed on a single dressing. Such inlet means may be a simple tube which passes fluid from the wound bed into the micropump. The inlet of the inlet tube may then need to be protected by a porous filter element. The inlet means may be a simple flexible tube or may be other means such as the fluid control articles described in U.S. Pat. No. 6,420,622 or the drain tubes described in U.S. Pat. No. 4,398,910.

Figure 18:
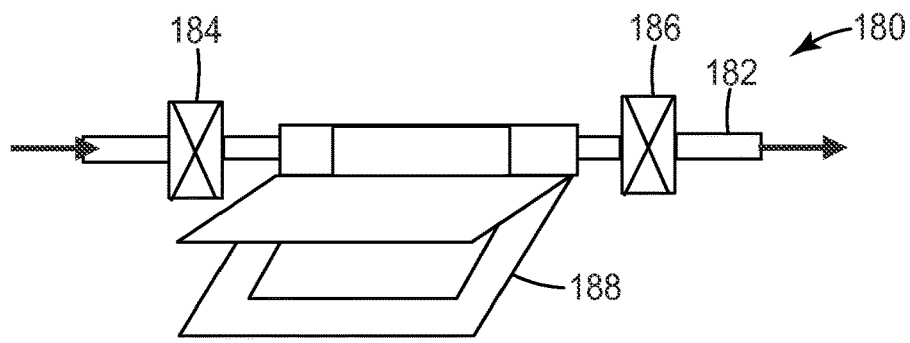
FIG. 18 is an exemplary embodiment of a tubular micropump.
Figure 20:
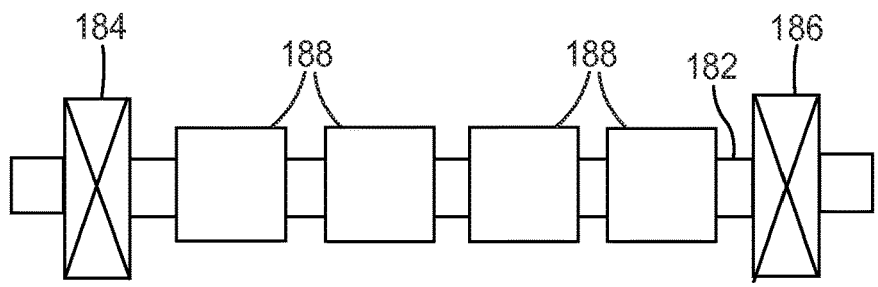
FIG. 20 is an exemplary embodiment of a diaphragm micropump.

When the micropump is not connected directly to the dressing it is preferably a tubular configuration such as micropump embodiments shown in FIGS. 18 and 20 that can be sealed between the dressing and the skin surface and pass between the wound bed (inlet) and the exterior.

The micropump exit is preferably in fluid communication with a reservoir further described below and designed to collect the excess wound fluid. The fluid reservoir may be a vented rigid container, a flexible container, or a vented flexible container. In a rigid container a vent is required in order to reduce or eliminate pressure build-up in the container. The container may be a simple vacuum canister such as used routinely in surgery, a canister or it may be a simple deflated flexible pouch that fills to capacity with excess wound fluid. The reservoir may be empty or may be filled with an absorbent that solidifies the fluid as it absorbed. Preferably the reservoir is a flexible pouch similar to that used in ostomy appliances and it may be flushable. It is a significant advantage of this invention in which the reservoir is filled under positive pressure that a rigid trap is not necessary, as opposed to vacuum systems which generally require rigid traps. Thus, the present invention can accommodate ambulatory patients by supplying a discrete system of a wound dressing, micropump and interchangeable small fluid reservoir collection pouches. The collection pouch can be constructed of any suitable polymeric material but is preferably an odor barrier such as disclosed in U.S. Pat. No. 7,270,860. Furthermore, the collection reservoir may have a means for alerting the patient or care giver that it should be changed. This alert can be an electronic means or a passive means.

Preferred fluid reservoirs can be a flexible pouch similar to that used in ostomy appliances such as those disclosed in U.S. Pat. No. 7,214,217. The pouches may even be flushable as disclosed in U.S. Pat. No. 7,179,245. However, the fluid reservoir may be as simple as a vacuum canister such as used routinely in surgery, a canister such as described in U.S. Pat. No. 4,569,674.

A sample port may be provided between the micropump and the fluid reservoir or on the reservoir itself for easily obtaining a sample for analysis. For example, a "T" shaped tubing may be provided in the exit line or a simple valved port on the fluid reservoir with a lure lock for attaching a syringe may be used. The sample can be used for analysis of chemical or physical properties of the wound fluid in order to assess healing or for further treatment means.

Wound Dressing Kits

Figure 17:
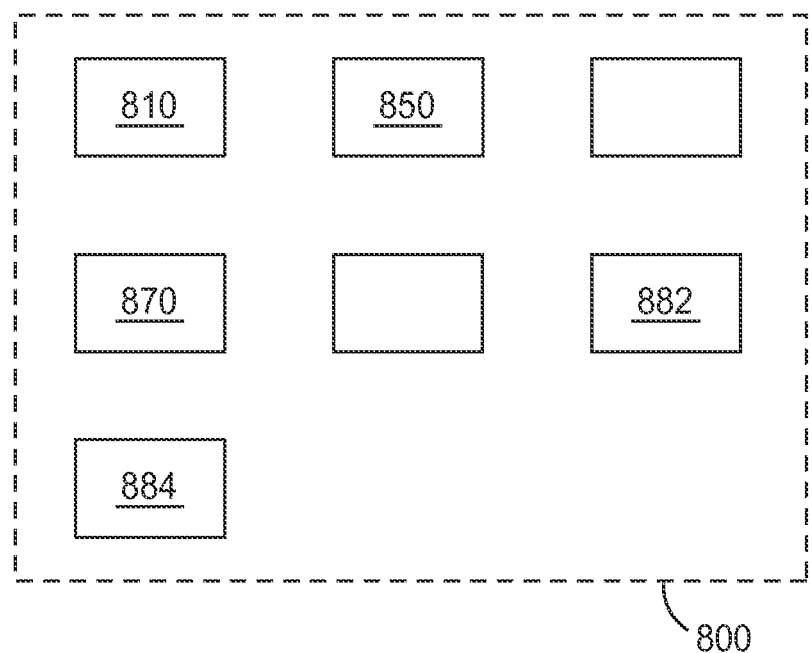
FIG. 17 is a block diagram of components that may be supplied in one exemplary embodiment of a wound dressing kit.

The wound dressings of the present invention may potentially be supplied in the form of a kit with one or more optional components. FIG. 17 is a schematic diagram of one kit 800. The kit 800 may preferably be provided in a sealed package (e.g., bag, pouch, tray, etc.). The kit 800 includes one or more wound dressings 810 of the present invention.

One or more micropumps 850 may also be provided in the kit 800, with the micropumps 850 attached to the wound dressing(s) 810 and/or provided as separate articles for the user to attach at their discretion and or one or more fittings 884 adapted for attachment to the external surfaces of the dressings 810 as discussed herein, where the fittings 884 can be used to provide connections between the wound dressing and/or valves in the dressings 810 and the micropumps 850. The kit 800 may also include one or more intermediate wound packing materials 870 as described herein.

The kit 800 may also include one or more fluid collection bags or cannisters 882 that may be used with the one or more micropumps 850 to collect fluids (e.g., liquids) that may be removed from sealed environments defined by the dressings 810 over wounds.

The following discussions will provide some non-limiting examples as to the various features that may be provided in the embodiments of the present invention.

Electroactive Polymer Films

The electroactive actuator displacement can be further increased by modifying the actuator structure. For example, mechanical structures that will enhance the displacement include multilayer laminates of electroactive materials, unimorph (e.g. a piezoelectric disk cemented to a thin metal disk), bimorph (e.g. a cantilever that consists of two active layers. For example, electrical activation of a piezoelectric bimorph cause one layer to extend and the other layer to contract), recurved benders, corrugated benders, spiral or helical designs. See, for example, Recurve Piezoelectric-Strain-Amplifying Actuator Architecture in IEEE/ASME TRANSACTIONS ON MECHATRONICS, VOL. 3, NO. 4, December 1998, 293, James D. Ervin and Diann Brei. Nonconductive polymer materials are described in U.S. Pat. Nos. 6,605,246, 6,343,129, and 5,977,585.

Nonconductive polymer actuator materials include fluoropolymers and polymers comprising silicone and acrylic moieties, and the like. Examples of fluoropolymers include homopolymers such as polyvinylidene difluoride (PVDF) copolymers such as polyvinylidene fluoride-trifluoroethylene P(VDF-TrFE), polyvinylidene fluoride-chlorofluoroethylene P(VDF-CFE), polyvinylidene fluoride-hexafluoropropylene P(VDF-HFP), polyvinylidene fluoride-trifluoroethylene-chlorofluoroethylene P(VDF-TrFE-CFE), polyvinylidene fluoride-trifluoroethylene-chlorotrifluoroethylene P(VDF-TrFE-CTFE), polyvinylidene fluoride-tetrafluoroethylene-chlorotrifluoroethylene, polyvinylidene fluoride-trifluoroethylene-hexafluoropropylene, polyvinylidene fluoride-tetrafluoroethylene-hexafluoropropylene, polyvinylidene fluoride-trifluoroethylene-tetrafluoroethylene, polyvinylidene fluoride-tetrafluoroethylene, polyvinylidene fluoride-trifluoroethylene-vinyl fluoride, polyvinylidene fluoride-tetrafluoroethylene-vinyl fluoride, polyvinylidene fluoride-trifluoroethylene-perfluoro(methyl vinyl ether), polyvinylidene fluoride-tetrafluoroethylene-perfluoro(methyl vinyl ether), polyvinylidene fluoride-trifluoroethylene-bromotrifluoroethylene, polyvinylidene fluoride-tetrafluoroethylene-bromotrifluoroethylene, polyvinylidene fluoride-tetrafluoroethylene-chlorofluoroethylene, polyvinylidene fluoride-trifluoroethylene-vinylidene chloride, and polyvinylidene fluoride-tetrafluoroethylene-vinylidene chloride. Other polymers include, polyurethane, silicone, fluorosilicone, natural rubber, polybutadiene, nitrile rubber, isoprene and combinations thereof.

Other suitable electroactive materials include: (a) Ceramic actuator material containing lead such as lead zirconate titanate (PZT), lead zirconate niobate:lead titanate (PZN:PT), lead magnesium niobate:lead titanate (PMN:PT), barium titanate ($BaTiO_3$); (b) Conductive polymers such as polyaniline, trans polyacetylene, polypyrrole, polythiophenes, polyethyldioxithiophene, carbon nanotubes etc.; (c) Ionic Polymer metal composite (IPMC) films, such as Nafion™ and Flemion™ or styrene/divinylbenzene, perfluorinated alkenes based polymers doped with metal ions such as $Pt(NH_3)_4HCl$; (d) Polymer gels actuators include polyacrylonitrile, polyacrylic acid gel, polyacrylic acid-poly vinylalcohal; and any combinations of the foregoing.

Backings

The wound dressings of the present invention are useful in connection with any conformable backing that provides a sufficiently impermeable barrier to the passage of liquids and at least some gases. Representative backings may include non-woven and woven fibrous webs, knits, films, foams polymeric films and other familiar backing materials. The preferred backing materials include thin elastomeric backings. These types of backings help ensure conformability and high adhesion around the wound site. Preferred backing materials may be translucent or transparent polymeric films including polyurethanes (e.g. ESTANE), polyether polyesters (e.g. HHTREL), polyether amides (e.g. PEGAX) as well as polyolefins (e.g. ENGAGE).

The backings used in connection with the present invention may be high moisture vapor permeable film backings. Issued U.S. Pat. Nos. 3,645,835 and 4,595,001 describe methods of making such films and methods for testing their permeability. The film (and any adhesive used thereon as described herein) may transmit moisture vapor at a rate equal to or greater than human skin. The adhesive-coated film may, e.g., transmit moisture vapor at a rate of at least 300 g/m²/24 hrs/37° C./100-10% RH, more preferably at least 700 g/m²/24 hrs/37° C./100-10% RH, and most preferably at least 2000 g/m²/24 hrs/37° C./100-10% RH using the inverted cup method as described in U.S. Pat. No. 4,595,001.

The backings may also preferably be conformable to anatomical surfaces. As such, when the backing is applied to an anatomical surface, it conforms to the surface even when the surface is moved. The backing may also be conformable to animal anatomical joints. When the joint is flexed and then returned to its unflexed position, the backing may stretch to accommodate the flexion of the joint, but is resilient enough to continue to conform to the joint when the joint is returned to its unflexed condition. A description of this characteristic of backings can be found in issued U.S. Pat. Nos. 5,088,483 and 5,160,315. Examples of some potentially suitable backings may include elastomeric polyurethane, polyester, or polyether block amide films. These films combine the desirable properties of resiliency, high moisture vapor permeability, and transparency.

Commercially available examples of potentially suitable backing materials may include the thin polymeric film backings sold under the tradenames TEGADERM (3M Company), BIOSITE (Johnson & Johnson Company), OPSITE (Smith & Nephew), etc. Many other backings may also be used, including those commonly used in the manufacture of surgical incise drapes (e.g., incise drapes manufactured by 3M Company under the tradename STERIDRAPE and IOBAN), etc.

Because fluids may be actively removed from the sealed environments defined by the wound dressings of the present invention, a relatively high moisture vapor permeable backing may not be required. As a result, some other potentially useful backing materials may include, e.g., metallocene polyolefins and SBS and SIS block copolymer (e.g., KRATON type) materials could be used.

Regardless, however, it may be preferred that the backings be kept relatively thin to, e.g., improve conformability. For example, it may be preferred that the backings be formed of (e.g., consist essentially of) polymeric films with a thickness of 200 micrometers or less, or 100 micrometers or less, potentially 50 micrometers or less, or even 25 micrometers or less.

Wound Packaging Material

In some embodiments, the wound dressings may be provided with wound packing material in as an intermediate layer. The wound packing material may, in some embodiments, also function as a filter element as described herein (although this function is not required). In some embodiments, the wound packing material may be resiliently compressible, such that the wound packing material can also optionally function as a ballast component to assist in maintaining a negative pressure in the sealed environment as described herein. For example, when a vacuum is applied the resilient packing will be compressed. When the vacuum is removed and the valve closed to seal the wound cavity the resilient packing will still provide an expansion force in order to return to its non-compressed state. This expansion will serve to create or help maintain a vacuum for a period of time. Wound packing materials may be useful where, e.g., the wound to be contained within the sealed environment is a chronic wound that is in the form of a significant depression (which may, in some instances be tunneled under the surrounding skin). When treating such wounds, it may be desirable to provide wound packing material in the wound before applying a wound dressing to create a sealed environment over the wound.

The wound packing material may preferably be flexible such that it can fill and/or conform to the shape of the wound. The wound packing may be absorbent or non-absorbent. The wound packing may preferably be capable of providing passageways through which fluids can pass. Some potentially suitable examples of wound packing materials may include fully or partially reticulated foam (e.g., open cell polyurethane foams, etc.), fabric (e.g., gauze, mesh, woven, knit, or nonwoven materials), particulate materials, beads, etc. that may be placed in a wound to fill the internal volume. If provided in particulate or bead form, the particulates or beads may, in some embodiments, be contained within a flexible bag or other structure to facilitate removal of the wound packing (unless, e.g., the wound packing material is bioabsorbable and/or biodegradable). A preferred polyurethane foam may be hydrophilic and capable of spontaneously absorbing deionized water such as WILSORB foam (available from Illbruck). Preferred hydrophilic packing components will absorb a 100 microliter drop of deionized water when gently placed in contact with the foam in less than 60 seconds and preferably in less than 30 seconds.

Polyvinylalcohol (PVA) open cell foams may also be used. A preferred fabric is nonwoven fabric and more preferably a lofted nonwoven fabric having resiliency such that when compressed to 50% of its thickness rebounds to 90% or greater of the original thickness in less than 10 seconds and preferably in less than 1 second. A preferred lofted resilient nonwoven has physical properties similar to 3M Buff Puff™ Facial Sponge. These structures may be treated to be hydrophilic and spontaneously wet with water. In some preferred embodiments the intermediate material may include several hydrophilic colloid materials to absorb fluids. In other embodiments the intermediate layers are preferably hydrophobic in order to retard tissue ingrowth. One skilled in the art will appreciate that there may be a number of materials suitable for the intermediate layer to achieve various objectives including combinations of the materials mentioned above and combinations that include other materials.

The intermediate layer can be secured directly to the dressing. For example, the intermediate layer can be secured via the pressure sensitive adhesive coating. In this embodiment the intermediate layer is placed at least over the portion of the dressing where the micropump inlet conduit will be located. This may be in the interior of the dressing or may be located at the periphery.

If the intermediate layer is provided in a form such that it is not attached to the wound dressing, the wound dressing may be provided in the form of a kit including the wound dressing and the separate barrier element and/or wound packing. In using such a kit, the barrier element and/or wound packing may be attached to the wound dressing before the wound dressing is delivered to a patient. Alternatively, the intermediate layer may be placed on or in the wound, with the wound dressing deployed over the wound after wound packing material is in position. The wound dressing 210 can be used according to methods for use with the other wound dressings, and includes the additional step of placing the intermediate material layer over at least a portion of the wound site.

Pressure Sensitive Adhesives

Suitable adhesive for use in wound dressing articles of the present invention include any adhesive that provides acceptable adhesion to skin and is acceptable for use on skin (e.g., the adhesive should preferably be non-irritating and non-sensitizing). Preferred adhesives are pressure sensitive and in certain embodiments preferably have a relatively high moisture vapor transmission rate to allow for moisture evaporation. Suitable pressure sensitive adhesives include those based on acrylates, polyurethanes, KRATON and other block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may preferably be used in the wound dressings of the present invention may include adhesives that are typically applied to the skin such as the acrylate copolymers described in U.S. Pat. No. RE 24,906, particularly a 97:3 iso-octyl acrylate:acrylamide copolymer. Another example may include a 70:15:15 isooctyl acrylate:ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

The pressure sensitive adhesives may, in some embodiments, transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used in the wound dressing may also include one or more areas in which the adhesive itself includes structures such as, e.g., the microreplicated structures described in U.S. Pat. No. 6,893,655.

Release Liners

Release liners may be supplied with the wound dressings of the present invention to protect the pressure sensitive adhesive used to attach the dressings to the patient and create the sealed environment. Release liners that may be suitable for use in the wound dressing of the present invention can be made of supercalendered kraft paper, glassine paper, polyethylene, polypropylene, polyester or composites of any of these materials. The liners are preferably coated with release agents such as fluorochemicals or silicones. For example, U.S. Pat. No. 4,472,480 describes low surface energy perfluorochemical liners. The liners may preferably be in the form of papers, polyolefin films, polyolefin coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Florchheim, (Florchheim, Germany). Another potential liner is silicone coated (1630) low density polyethylene available from Huhtamaki.

The selection of a specific release liner may be made in conjunction with the selection of a pressure sensitive adhesive. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

Carriers/Delivery Systems

In some instances, the backings used in the wound dressings of the present invention may be so flexible and supple such that when a release liner is removed from the backing, the backing may tend to fold and adhere to itself, interfering with the smooth, aseptic application of the dressing to a patient's skin.

Various delivery systems have been proposed to address this problem such as those disclosed in U.S. Pat. No. 4,485,809; 4,600,001; and EP Publication No. 0 051 935. Carrier-type delivery systems such as those described in U.S. Pat. No. 6,685,682 offer an alternative delivery system for use with conformable backings.

Alternative carriers and/or delivery systems may include frames, handles, stiffening strips, etc. as disclosed in issued U.S. Pat. Nos. 6,742,522; 5,979,450; 6,169,224; 5,088,483; 4,598,004; D 493,230; etc. Still another potentially suitable delivery system may be described in U.S. Patent Application Publication No. US 2007/0156075 A1. In some instances, the backings can be delivered linerless as described in, e.g., U.S. Pat. No. 5,803,086.

EXAMPLES

Exemplary embodiments of this invention are discussed and reference has been made to possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention will be further clarified by the following examples which are exemplary and not intended to limit the scope of the invention.

Example 1

Figure 15:
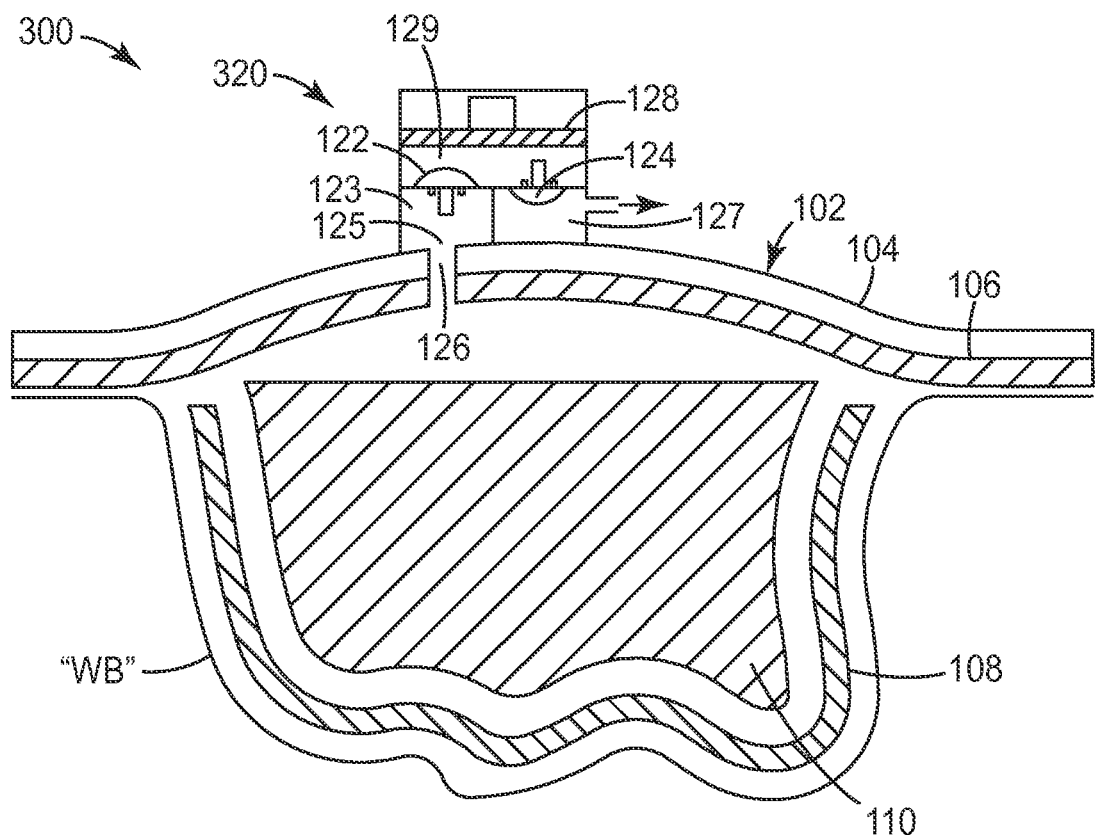
FIG. 15 is a schematic view of the wound dressing and micropump system, wherein the micropump is mounted on the wound dressing.

FIG. 15 is a cross-sectional schematic diagram of this example. A Tegaderm™ (3M Company, Maplewood Minn.) wound dressing 102 is used to seal a wound cavity defined by the wound bed "WB" and the wound dressing. The wound cavity is filled with a wound packing 110. A diaphragm micropump is fixed to the exterior surface of the wound dressing backing. The micropump extracts fluid (air and wound exudate) and moves this fluid through the exudate collection line to a to a flexible collection pouch 150. Although shown with a single micropump multiple micropumps may be used over a single wound site. The collection pouch is designed very similar to an ostomy bag and can be worn in a similar manner. The collection pouch may be sealed or vented. In a preferred embodiment it is not vented. If vented, it may include a vent filter to reduce order that may be generated from the wound fluid. A valve is placed in the exudate collection line 140 which may be used to collect samples of wound fluid for analysis.

Figure 16:
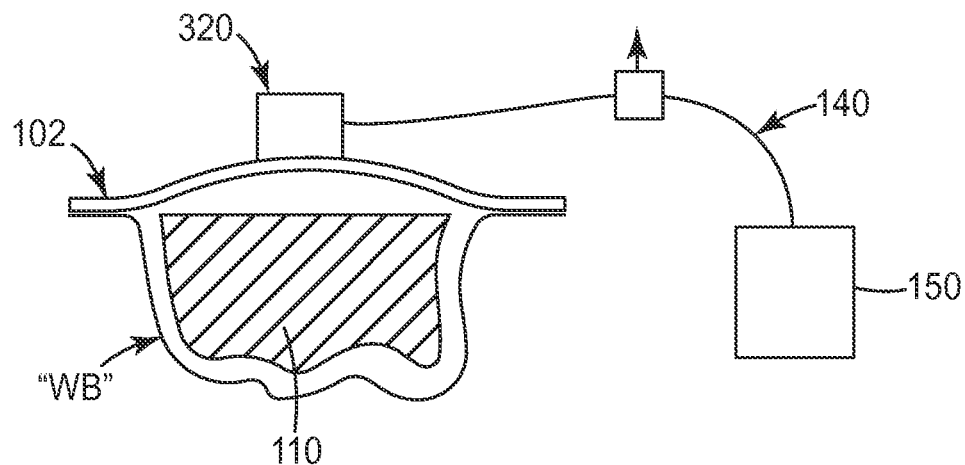
FIG. 16 is a view similar to the view of FIG. 3 illustrating the wound dressing and micropump system wherein the micropump is in fluid communication with the wound dressing.

Referring to FIGS. 15 and 16, the wound evacuation system 300 is comprised of wound dressing 102, a base layer 108, a wound packing 110, a micropump 320, an evacuation line 140, and a wound fluid collection pouch 150. The wound dressing, 102, is comprised of an elastomeric polyurethane film and adhesive as described in U.S. Pat. Nos. 5,088,483 and 5,738,642. As supplied the dressing further comprises a disposable release liner (not shown) that protects the pressure sensitive adhesive (PSA), 106. The PSA, 106, is coated continuously over the entire surface of the wound dressing backing, 104. An orifice, 126, is made through the dressing that communicates with pump inlet opening 125. The pump inlet 125 of the micropump leads to a chamber, 123, having a self sealing elastomeric one-way inlet valve, 122. Fluid enters the inlet chamber passes into a pumping chamber 129 and exits through the exit chamber 127. An exit valve, 124, is placed at the entrance to the outlet chamber. The one-way inlet and exit valves are shown as an elastomeric umbrella valve which may be obtained from Vernay Laboratories, Yellow Springs, Ohio. Both umbrella valves are normally closed valves. Although shown with a single inlet and outlet valve, multiple inlet and multiple outlet valves may be used. Importantly, we have found that the inlet and outlet valves need to have a "cracking pressure". That is, a finite minimum pressure which causes them to open. This ensures a good seal. Without a good tight hermetic seal the micropump will not operate at low flow rates. Thus, the umbrella valve elastomeric stem is designed to be stretched to provide a strain force sufficient to bias the valves into a normally close condition. Alternatively, duck bill valves may be used that have a defined cracking pressure. Duckbill valves also are available from Vernay Laboratories. The micropump also includes a diaphragm, 128, that is capable of displacement sufficient to move the fluid. The diaphragm is made of a thermoplastic polymer, thermoset polymer, ceramic, metal, or combination thereof such as a laminate. The diaphragm is necessarily resilient and will fully and rapidly recover from any induced strain. Strain (displacement) is induced by the use of an actuator. The actuator can be a solenoid, piezoelectric ceramic such as PZT, a voice coil or an "internal actuator". The internal actuator means that at least a portion of the diaphragm itself can function as an actuator. In one embodiment the internal actuator is a polyurethane material as disclosed in U.S. Pat. No. 5,977,685. In an alternative preferred embodiment the internal actuator is a multilayer electroresponsive polymer membrane (EPM) as described herein. Alternatively, the valves (122 and 124) and diaphragm, 128, may be eliminated and replaced with a digital pulse activated actuated pump system as described in U.S. Patent Application Publication No. 2004/0234401 in which multiple actuators are in direct contact with the fluid. A preferred piezoelectric micropump is a $\frac{1}{10}$ scale version of a Model BPH-414D piezoelectric pump available from MEDO USA.

This micropump is capable of pulling a vacuum of 161 mmHg below atmospheric pressure without the need for priming. It is a desired property of the micropumps that they be self-priming (i.e. no priming necessary).

Alternatively the wound micropump can be made using a conductive polymer diaphragm internal actuator as described in WO2005/042974 A1 and JP04015832. In this design the conductive polymer is driven to expand and contract by a chemical electrolytic mechanism requiring low voltage (e.g. less than 5 volts DC and typically 1-2 Vdc). Like the EAP and digital pulse activated pump systems this type of actuator is silent allowing the micropump to make very little, if any, noise.

Multiple cells with smaller diaphragms may also be used to generate higher inlet vacuum and higher exit pressure.

In operation, a battery sends current to the actuator which causes the diaphragm to displace up, down, or both up and down. This movement displaces the fluid in the pumping chamber creating a positive pressure at the exit valve and a negative pressure at the inlet valve. In one embodiment the maximum vacuum (i.e. pressure less than atmospheric) is self limiting as determined by the actuator and valving parameters and is preset so the clinician does not have to worry about it. Alternatively, a controller may be provided that can allow the clinician to adjust the flow rate and/or vacuum created. The battery may be a disposable battery such as a common watch, AAA, AA, alkaline battery, a lithium ion battery, a lithium polymer battery, nickel cadmium battery, nickel metal hydride battery, and the like. It may be disposable or rechargeable. One or more batteries may be used and arranged in series or in parallel. A transformer or converter may be used in order to drive a direct current (DC) or alternating current (AC) actuator. The battery is preferably secured to the patient at a location where they will not lie on it creating a potential pressure point. Once the micropump is activated it is self priming and a vacuum will be applied to the wound cavity. The dressing shown in FIGS. 15 and 16 will likely be sucked into the wound. This will be supported by the wound packing material 110. Preferred wound packing materials include hydrophobic open cell polyurethane foam, open cell hydrophilic polyurethane foam such as Aquazone foam available from Foamex International, Linwood, Pa. Foams may have pore sizes of 30-200 pores per inch but are preferably 50-150 PPI. Densities may be from 1 to 5 lb/ft$^3$ (16-80 kg/M$^3$) but are preferably 1.5 to 3 lb/ft³ (25-50 kg/M³). When sufficient fluid has filled the wound packing it will begin to enter the micropump and subsequently be delivered through the evacuation line 140 to the wound fluid collection pouch 150. Alternatively, the wound packing material is a resilient nonwoven such as 3M Buff Puff™ (3M Company, Maplewood, Minn.). When the pouch becomes full a new pouch with integral evacuation line may be attached to the micropump. Alternatively, the pouch may be adapted to allow removal and attachment of the evacuation line. Preferably the pouch can be easily emptied into a toilet or other secure disposal. The collection pouch also may incorporate a superabsorbent polymer that gels the wound fluid as it enters the pouch. In this manner, the pouch can be disposed of in regular trash without concern of leakage. The pouch also may contain more or more antimicrobial agents to kill any bacteria and prevent odor. Similarly, the wound packing material may contain an antimicrobial agent or other medicament suitable for treating wounds.

The wound dressing system also may comprise a wound contact layer 108. The wound contact layer may be a separate component but preferably is bonded to the wound packing material. Bonding may be accomplished by thermal or adhesive methods. FIG. 5 shows the wound contact layer as a separate component. Suitable wound contact layers include Tegapore™, (3M Company, Maplewood, Minn.) or XEROFLO™ (Kendall Corp. a division of Covidien, Mansfield, Mass.). Other suitable wound contact layers include gels such as alginate gels and alginate fabrics such as Tegaderm™ Alginate (3M Company, Maplewood, Minn.) or carboxymethylcellulose nonwoven fabrics such as Aquacel Ag (Convatec a division of E. R. Squibb & Sons, LLC, UK)

Example 2

The wound dressing evacuation system of Example 1 is employed except that the micropump is supplied separately in a kit with the wound dressing. The kit comprises the micropump, wound dressing, wound packing material with an integral (bonded) wound contact layer, evacuation line and wound fluid exudate collection pouch. As in Example 1, the wound packing/contact layer is cut to size and placed in the wound. The dressing is placed over the entire wound making certain to seal well to the surrounding tissue and forming a hermetic seal. The micropump comprises a pressure sensitive adhesive on its base. The micropump is positioned over the preformed orifice in the dressing (126). In this embodiment the micropump may be reusable (but preferably only on a single patient) and applied to several dressings in succession as needed.

Example 3

The wound dressing evacuation system of Example 2 is employed except that the dressing is not supplied with an orifice. Instead the orifice is created by the clinician using a supplied punch which may be similar in operation to a hand held paper hole punch. The orifice may be placed anywhere on the dressing the clinician prefers such as in the center or along the periphery. Multiple orifices and multiple micropumps are employed.

Example 4

The wound dressing evacuation system of Example 1 is employed. The housing of the micropump must be rigid enough to prevent it from collapsing during operation. Thus, this can create a pressure point. In order to prevent further tissue damage in a patient who may lie on the wound the micropump is sealed in a conformable elastomer which acts as a cushioning device and prevents sharp pressure points.

Example 5

The wound dressing evacuation system of Example 2 is employed except that the wound dressing is supplied with a vacuum valve over the orifice. A film laminate vacuum valve is used such as that described in PCT Publication WO2009/124125 and incorporated by reference in its entirety. A preferred valve is which is commercially used on Reynolds Handi-Vac vacuum freezer bags (Alcoa Inc., Richmond, Va.).

Example 6

The wound dressing evacuation system of Example 1 is employed except that the wound dressing is further augmented with an absorbent layer in combination with a hydrophobic foam packing. The absorbent layer is a hydrogel such as that used in the dressings of U.S. Pat. No. 7,005,143.

Example 7

The wound dressing evacuation system of Example 2 is employed except that the micropump is placed off the dressing and adhered to the skin or to a separate secural device. The micropump is connected to the wound dressing through an inlet line (tubing) and a port which is secured to the dressing over the orifice with, for example, an adhesive, heat seal, or solvent weld.

Example 8

The wound dressing evacuation system of Example 1 is employed except that the wound dressing further comprises a frame on the perimeter of the top surface in order to facilitate delivery as described in U.S. Pat. Nos. 5,088,483 and 5,738,642 which are incorporated herein by reference.

Example 9

The wound dressing evacuation system of Example 1 is employed except that the wound dressing further comprises a microreplicated fluid control feature on the inner (wound facing) surface in order to facilitate transport of excess fluid to the micropump. Dressings incorporating microreplicated fluid control features are described in U.S. Pat. No. 6,420,622 which is incorporated herein by reference.

Example 10

Figure 19:
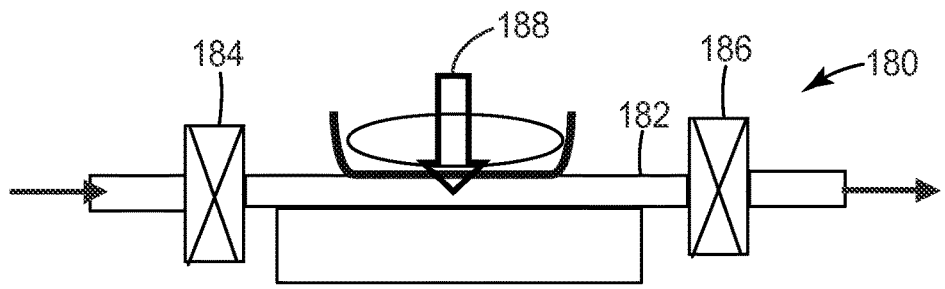
FIG. 19 is an exemplary embodiment of a tubular micropump.

The wound dressing evacuation system of Example 7 is employed except that a tubular micropump 180 is employed. The tubular micropump comprises a section of elastomeric tubing 182 separated by a one way inlet valve (e.g. a duckbill valve) 184 and a one way exit valve 186. Along the tubing section is one or more means 188 of depressing or squeezing the tubing to partially or completely collapse the walls together at one or more points along the tubing section. This may be accomplished using any of the actuators described in Example 1. This is distinct from a peristaltic pump which using a rotating series of rollers to sequentially depress and move fluid along the tubing without valves. Examples of tubular micropumps are shown in FIGS. 18-20.

Example 11

Elastomeric Electro Active Polymer Pump 210

The commercially available VHB-4910 and 4905 tapes from 3M Company (Maplewood Minn.) were used as an actuator film (pump diaphragm) 212. The actuator film was stretched 400% in the plane of the film (XY direction).

The film was kept pre-stretched by stretching in over and securing it to a glass ring. Due to sticky nature of VHB tape, no other tape was use to stick the VHB to glass ring and also to make multilayer actuator films. The gold electrode was coated on the both sides of pre-stretched film using Pelco SC-6 sputter coater. A paper circular mask was used to get desired shape (2.5 cm and 4 cm diameter) of the gold electrode. The strip of 20 mm×20 mm of 3M 1181 copper conductive tape was used to make connections at the edge of each gold coating.

In the case of multilayer actuator films, the first actuator film is coated as explained above. The second actuator film was stretched 400% in both directions and than carefully laminated to first layer. The top electrode of first layer is used as a bottom electrode of $2^{nd}$ layer. A strip of copper tape was attached to the gold electrode before laminating another layer.

After producing the desired multilayer actuator, polyurethane (Tegaderm 1621) was laminated on the top of the actuator stack. The polyurethane film 212 did not have any electrode on the top. This film was then removed from glass ring and laminated to the top cover of a pump housing. The top cover 214 was placed on the bottom of the pump housing with the polyurethane layer down.

The multilayer actuator diaphragm was activated (induced to move in the Z axis) by applying a AC voltage using Trek model #610E voltage amplifier connected with function generator HP 3314A. The 10 mmHg pressure was achieved using 5-layers of VHB and One layer of polyurethane film.

Figure 21:
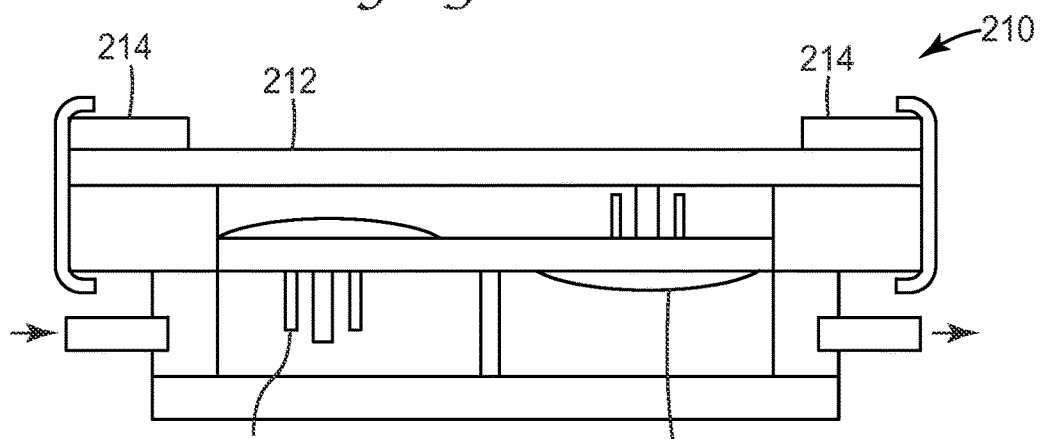
FIG. 21 is an exemplary embodiment of an electroactive polymer pump.

The arrangement produced is shown in FIG. 21. One way valves 216, 218 allow liquid to go in an out.

Examples 12 and 13

Alternative Pump Designs

Example 12

Conductive Polymer Pump

A conductive polymer micropump useful in this invention is commercially available from EAMEX Corporation, Osaka Japan and has an actuator comprising a modified polypyrrol polymer—(PPy-$CF_3SO_3$). The micropump specifications of a few of these micropumps are described below.

| Size | 25 × 22 × 3 mm | 27 × 4 mm | 30 × 6 mm |
|---|---|---|---|
| Diameter of diaphragm | φ4 mm | φ10 mm | φ24 mm |
| Number of cells | 19 | 4 | 1 |
| Pressure | 70 kPa | 55 kPa | 40 kPa |
| Flow | 0.9 ml/min | 3 ml/min | 6 ml/min |
| Frequency | 1 Hz | 1 Hz | 1 Hz |
| Voltage | 2 V | 2 V | 2 V |
| Current | 200 mA | 200 mA | 200 mA |

Example 13

Piezoelectric Ceramic Pump

A piezoelectric micropump was purchased from BIMOR Pump, model #BPH-414D serial #30805146 was purchased from MEDO USA Inc, Hanover Park, Ill., 60103 (http://www.nitto-europe.com/german/pumps/bimor/index.html). The inlet pressure of 161 mmHg was measured. This micropump was approximately 7.5×6.8×2.5 cm in diameter. Thus, a ⅓ to 1/10 scale model smaller micropump would be particularly useful in the present invention.

Another piezoelectric micropump model #DTI-200-12.5P was purchased DEAK Technologies Inc., Brooklyn, N.Y. The piezoelectric material is used for both piezoelectric micropumps is PZT. This micropump has the following dimensions:
Pump: 4.25 cm dia., Mounting flange, 6.25 cm dia., Height: 2.5 cm. A smaller ½ to ⅕ scale model of this micropump is preferred for the present invention.

The complete disclosure of the patents, patent documents, and publications cited herein are incorporated by reference in their entirety as if each were individually incorporated (although conflicts between any such disclosures and the descriptions explicitly provided herein should be resolved in favor of this document).

The invention claimed is:
1. A wound dressing apparatus, which comprises:
a wound dressing comprising a backing having an interior surface configured to face a wound and an exterior surface opposite the interior surface, the interior surface of the backing comprising an adhesive area that forms a sealed environment between the interior surface and the wound, and a non-adhesive area comprising a stand-off element, the stand-off element comprising structures defining a plurality of fluid channels; and
a micropump system including a rotorless, self-priming micropump mounted to the exterior surface of the backing such that the micropump is integral with the wound dressing, the micropump comprising an electroactive actuator member, a first chamber for applying subatmospheric pressure to the sealed environment around the wound, and a second chamber for output pressure above atmospheric pressure;
wherein fluid enters an inlet side of the micropump to the first chamber through a normally closed one-way inlet valve, wherein the inlet valve is located in the non-adhesive area or proximate a perimeter of the non-adhesive area, enters the second chamber through a normally closed one-way outlet valve, and exits the second chamber of the micropump to a fluid accumulation device when the sealed environment is under positive pressure relative to the atmosphere, and wherein the channels in the stand-off element maintain removal of the fluid through the inlet valve when the sealed environment is under negative pressure relative to the atmosphere.
2. The wound dressing apparatus according to claim 1, wherein the wound dressing apparatus further includes an exudate collection line and an exudate collection device.

3. The wound dressing apparatus according to claim 2, wherein the exudate collection device is a flexible disposable pouch.

4. The wound dressing apparatus according to claim 1, wherein a vacuum applied by the micropump is self-limiting and incapable of creating a vacuum in excess of 200 mmHg below atmospheric pressure.

5. The wound dressing apparatus of claim 1, wherein the adhesive area comprises an adhesive that extends around a perimeter of the interior wound facing surface of the backing to adhere the wound dressing to a subject over a wound.

6. The wound dressing apparatus of claim 1, wherein the normally-closed inlet valve is attached to the backing over an opening formed through the backing, wherein fluid flow through the opening is controlled by the normally-closed valve, and wherein a dead volume between the normally-closed valve and the backing is 10 mm$^3$ or less.

7. A wound dressing apparatus according to claim 6, wherein the normally-closed inlet valve comprises a one-way valve that permits fluid flow out of the sealed environment when in an open configuration and restricts fluid flow into the sealed environment when in a closed configuration.

8. A wound dressing apparatus according to claim 6, wherein the normally-closed inlet valve comprises a plurality of polymeric film layers aligned with the backing, and wherein the plurality of polymeric film layers comprises a flap layer comprising a flap formed therein, wherein the flap is selectively moveable to transform the inlet valve from a closed configuration to an open configuration.

9. The wound dressing apparatus of claim 1, wherein the micropump has an actuator dimension of less than 10 cm$^2$.

10. The wound dressing apparatus of claim 1, wherein the micropump is driven by AC or DC power.

11. The wound dressing apparatus of claim 1, further comprising a battery power source for the micropump.

12. The wound dressing apparatus of claim 1, wherein the micropump comprises an electroactive activator member comprising is made using an electroactive diaphragm.

13. The wound dressing apparatus of claim 12, wherein the electroactive diaphragm is piezoelectric or electrorestrictive.

14. The wound dressing apparatus of claim 1, wherein the micropump comprises an electroresponsive element, a pair of electrodes capable of applying a voltage potential across a thickness of at least a portion of the electroresponsive element, and a power supply capable of applying the appropriate voltage drop to attain a required compression.

15. The wound dressing apparatus of claim 1, wherein the backing further comprises an absorbent material.

16. A wound dressing apparatus, which comprises:
a wound dressing comprising a backing having an interior surface configured to face a wound and an exterior surface opposite the interior surface, the interior surface of the backing comprising an adhesive area of an adhesive dimensioned to form a perimeter around the wound and configured to form a sealed environment between the interior surface and the wound, and a non-adhesive area comprising a stand-off element, the stand-off element comprising structures defining a plurality of fluid channels; and
a micropump system comprising a rotorless, self-priming micropump attached to the backing over an opening formed in the backing, the micropump comprising:
an electroresponsive element comprising a multilayer film comprising alternating conductive polymeric layers and nonconductive polymeric layers, a pair of electrodes capable of applying a voltage potential across a thickness of at least a portion of the electroresponsive element, and a power supply;
a first chamber for applying subatmospheric pressure to the sealed environment, and
a second chamber for output pressure above atmospheric pressure;
wherein fluid enters an inlet side of the micropump to the first chamber through a normally closed one-way inlet valve in the non-adhesive area, the inlet valve comprising a plurality of polymeric film layers aligned with the backing, wherein the plurality of polymeric film layers comprises a flap layer comprising a flap formed therein, wherein the flap is selectively moveable to transform the inlet valve from a closed configuration to an open configuration; enters the second chamber through a normally closed one-way outlet valve, and exits the second chamber of the micropump to a fluid accumulation device when the sealed environment is under positive pressure relative to the atmosphere, and wherein the channels in the stand-off element maintain removal of the fluid through the inlet valve when the sealed environment is under negative pressure relative to the atmosphere.

* * * * *

UNITED STATES PATENT AND TRADEMARK OFFICE
CERTIFICATE OF CORRECTION

PATENT NO. : 10,653,823 B2
APPLICATION NO. : 14/721157
DATED : May 19, 2020
INVENTOR(S) : Vivek Bharti It is certified that error appears in the above-identified patent and that said Letters Patent is hereby corrected as shown below:

In the Specification

Column 7
Line 25          Delete "mmHg" and insert -- mmHg. --, therefor.

Column 15
Line 64          Delete "priming" and insert -- priming. --, therefor.

Column 16
Line 28          Delete "electroresponseive" and insert -- electroresponsive --, therefor.
Line 39          Delete "Zetpole," and insert -- Zetpol, --, therefor.
Line 28          Delete "Alterntatively," and insert -- Alternatively, --, therefor.

Column 24
Line 11          Delete "polyphthaloxyanine," and insert -- polyphthalocyanine, --, therefor.

Column 26
Line 9           Delete "ionic" and insert -- Ionic --, therefor.
Line 9           Delete "(IMPC)" and insert -- (IPMC) --, therefor.
Lines 25-26      Delete "/trifluoroethyelne" and insert -- /trifluoroethylene --, therefor.

Column 28
Line 11          Delete "and or" and insert -- and/or --, therefor.

Column 29
Lines 2-3        Delete "polybutadine," and insert -- polybutadiene, --, therefor.
Line 10          Delete "polyethyldioxithiophene," and insert -- polyethylenedioxythiophene, --, therefor.
Line 16          Delete "vinylalcohal;" and insert -- vinylalcohol; --, therefor.
Line 29          Delete "HHTREL)," and insert -- HYTREL), --, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,653,823 B2

Column 32
Line 32   Delete "Florchheim, (Florchheim, Germany)." and insert -- Forchheim, (Forchheim, Germany). --, therefor.

Column 37
Line 43   Delete "an" and insert -- and --, therefor.
Line 59   Delete "polypyrrol" and insert -- polypyrrole --, therefor.

In the Claims

Column 39
Line 38   In Claim 12, before "an" delete "is made using".